US008021528B2

(12) United States Patent
Jang

(10) Patent No.: US 8,021,528 B2
(45) Date of Patent: Sep. 20, 2011

(54) BIOSENSOR

(76) Inventor: Yong-Sang Jang, Yongin-shi (KR)

( * ) Notice: Subject to any disclaimer, the term of this patent is extended or adjusted under 35 U.S.C. 154(b) by 814 days.

(21) Appl. No.: 12/043,375

(22) Filed: Mar. 6, 2008

(65) Prior Publication Data

US 2008/0217171 A1 Sep. 11, 2008

(30) Foreign Application Priority Data

Mar. 7, 2007 (KR) .................... 10-2007-0022664

(51) Int. Cl.
*G01N 27/26* (2006.01)
*G01N 27/327* (2006.01)

(52) U.S. Cl. ............... 204/403.14; 204/403.11; 205/792

(58) Field of Classification Search .............. 204/403.01–403.15; 205/775, 205/777.5, 778, 792; 600/345–348; 422/400–430, 422/500–570
See application file for complete search history.

(56) References Cited

U.S. PATENT DOCUMENTS

| | | | | |
|---|---|---|---|---|
| 5,437,999 | A | * | 8/1995 | Diebold et al. .......... 204/403.11 |
| 6,287,451 | B1 | | 9/2001 | Winarta |
| 2002/0027072 | A1 | * | 3/2002 | Cui et al. ...................... 204/403 |
| 2003/0061687 | A1 | | 4/2003 | Hansen |
| 2004/0040866 | A1 | * | 3/2004 | Miyashita et al. ......... 205/777.5 |
| 2005/0000808 | A1 | * | 1/2005 | Cui et al. .................. 204/403.14 |
| 2006/0042943 | A1 | * | 3/2006 | Shiraki et al. .............. 204/403.1 |

FOREIGN PATENT DOCUMENTS

| | | |
|---|---|---|
| KR | 10-2002-0088521 A | 11/2002 |
| KR | 10-2003-0054204 A | 7/2003 |
| KR | 10-2004-0105429 A | 12/2004 |

* cited by examiner

*Primary Examiner* — Jeffrey T Barton
*Assistant Examiner* — Jennifer Dieterle
(74) *Attorney, Agent, or Firm* — Lexyoume IP Group, PLLC.

(57) ABSTRACT

A biosensor that is capable of measuring a material contained in a sample is provided. The biosensor is configured to be inserted into a display device, and measures a material contained in the sample. The biosensor includes i) first and second substrates that are opposed to each other; ii) a sample guiding layer that has two sample injection openings and is located on the first substrate; iii) a first electrode that is located between the first substrate and the sample guiding layer; iv) a second electrode that is located between the second substrate and the sample guiding layer; v) a third electrode that is located between the sample guiding layer and the second substrate; and vi) a penetrated opening that penetrates the first substrate, the sample guiding layer, and the second substrate. The second electrode is spaced apart from the first electrode. The biosensor further includes i) a long edge, and ii) a short edge that shares a corner of the biosensor and neighbors the long edge. Each of the two sample injection openings is formed to correspond to the long edge and the short edge, respectively.

16 Claims, 20 Drawing Sheets

BIOSENSOR

CROSS-REFERENCE TO RELATED APPLICATION

This application claims priority to and the benefit of Korean Patent Application No. 10-2007-0022664 filed in the Korean Intellectual Property Office on Mar. 7, 2007, the entire contents of which are incorporated herein by reference.

BACKGROUND (a) Field of the Invention The present invention relates to a biosensor. More particularly, the present invention relates to a biosensor for detecting a target material from a blood sample.

(b) Description of the Related Art

In general, biosensors such as blood glucose meters use an electrochemical method. The electrochemical detecting method generally involves a structure in which an enzyme and a mediator are immobilized in a cell consisting of an anode and a cathode. When a sample is introduced to the inside of such a biosensor, the target material in the sample is oxidized by the catalytic action of an enzyme, while oxygen or an electron transfer medium is reduced. Here, the reduced oxygen or electron transfer medium is oxidized under compulsion by the voltage of the electrode to cause changes in electrons. A method of quantifying such changes in electrons and indirectly measuring the amount of the target material is referred to as an electrochemical detecting method.

Since such biosensors use blood as a specimen, the biosensors are subject to interference depending on the types of blood. Furthermore, there is a need to develop a biosensor that uses smaller blood samples, and that can make measurements more rapidly, more conveniently, and more accurately.

SUMMARY

The present invention has been made in an effort to provide a biosensor that is capable of using a smaller sample, and to provide accurate and convenient measurement while avoiding problems caused by various blood types and interference.

According to an embodiment of the present invention, the biosensor is configured to be inserted into a display device and measures a material contained in the sample. The biosensor includes: i) first and second substrates that are opposed to each other; ii) a sample guiding layer that has two sample injection openings and is located on the first substrate; iii) a first electrode that is located between the first substrate and the sample guiding layer; iv) a second electrode that is located between the second substrate and the sample guiding layer; v) a third electrode that is located between the sample guiding layer and the second substrate; and vi) a penetrated opening that penetrates the first substrate, the sample guiding layer, and the second substrate. The second electrode is spaced apart from the first electrode. The biosensor further includes i) a long edge, and ii) a short edge that shares a corner of the biosensor and neighbors the long edge. The two sample injection openings are formed to correspond to the long edge and the short edge, respectively.

The biosensor according to an embodiment of the present invention may further include a fourth electrode that is located on the first substrate to be exposed to the outside. The fourth electrode may be spaced apart from the first electrode along a direction that is configured for the biosensor to be inserted into the display device. The fourth electrode may be located to be closer to the display device than the first electrode when the biosensor is inserted into the display device.

The display device may include i) a first connector pin, and ii) a second connector pin that has a greater length than that of the first connector pin and is spaced apart from the first connector pin to be extended parallel to the first connector pin. The display device may display an error message when the first connector pin is connected to the fourth electrode and the second connector pin is connected to the first electrode. The display device may include i) a first connector pin, and ii) a second connector pin that has a greater length than that of the first connector pin and is spaced apart from the first connector pin to be extended to be parallel to the first connector pin. The amount of the material may be displayed when the first and second connector pins are electrically connected to the third electrode.

The first electrode may include i) a first body portion, ii) a first connecting portion that is connected to the body portion and neighbors the fourth electrode, and iii) a sample contacting portion that is connected to the first connecting portion and is configured to contact the sample. The first connecting portion may be configured to be electrically connected to the display device and to be extended along a direction in which the biosensor is inserted into the display device. The third electrode may include i) second body portion, and ii) second connecting portion that is connected to the second body portion. The second connecting portion may be configured to be electrically connected to the display device to be extended along a direction in which the biosensor is inserted into the display device. The first connecting portion and the second connecting portion may be exposed to the outside in opposite directions to each other, and the second electrode is located between the first connecting portion and the second connecting portion. The first connecting portion and the second connecting portion may be located such that they are symmetrical to each other based on the second electrode along a direction that perpendicularly crosses the direction in which the biosensor is inserted into the display device. The sample guiding layer may further include two sample guiding channels that connect the two sample inlets with a hole. The second electrode may include two branched portions that meet with each of the two sample guiding channels. Each of the two branched portions may be spaced apart from the sample contacting portion, respectively. Each of the two branched portions may be located to be closer to the hole than the sample contacting portion along the two sample guiding channels, respectively.

The sample guiding layer may further include a sample guiding channel that connects a sample inlet that corresponds to the long edge with the hole. The sample guiding channel may be bent. The sample inlet corresponding to the long edge may be located to be closer to the fourth electrode than the penetrated opening. The sample guiding layer may further include another sample guiding channel that connects a sample inlet that corresponds to the short edge with the hole. The sample guiding channel and the other sample guiding channel may be connected to the penetrated opening at both sides of the penetrated opening opposite to each other.

The sample guiding layer may further include a sample guiding channel that connects the sample inlet with the penetrated opening. A mediator may be located in the sample guiding channel. The mediator may include i) an enzyme that reacts with the material, ii) an electron transfer medium that transfers electrons generated from the enzyme, and iii) a dispersion stabilizer that disperses and stabilizes the enzyme and the electron transfer medium.

The enzyme may be at least one selected from the group consisting of glucose oxidase, glucose dehydrogenase, alcohol oxidase, alcohol dehydrogenase, pyrroloquinone (PQQ), and nicotinamide adenine dinucleotide/hydrogen (NAD/

NADH). The electron transfer medium may be at least one selected from the group consisting of ferrocene, quinone, cobalt, nickel, ruthenium, a ferricyan compound, rhodium, palladium, osmium, iridium, platinum, hexaammineruthenium (III) chloride, derivatives including these, and transition metals. The dispersion stabilizer may be at least one selected from the group consisting of polyvinyl alcohol, polyethylene oxide, polyethylene glycol, carboxymethyl cellulose, hydroxymethyl cellulose, 2-hydroxyethyl cellulose, hydroxypropyl cellulose, microcrystalline cellulose, polyvinyl pyrrolidone, polyvinylidene fluoride, polymethyl methacrylate, and styrene butyl rubber.

The mediator may further include a surfactant. The surfactant may include at least one selected from the group consisting of anionic surfactants, cationic surfactants, amphoteric surfactants, and nonionic surfactants. The anionic surfactant may include a soap or alkylbenzene sulfonate. The mediator may further include a phase transfer catalyst. The phase transfer catalyst may include at least one selected from the group consisting of phosphonium-based reagents, crown ether-based reagents, ammonium-based reagents, and polyethylene glycol (PEG)-based reagents. The mediator may further include glucose oxidase, hexaammineruthenium(III) chloride, carboxymethyl cellulose, microcrystalline cellulose, tricaprylmethyl ammonium chloride, t-octylphenoxypolyethoxyethanol, and a soap.

According to another embodiment of the present invention, the biosensor includes: i) a first substrate; ii) an adhesive cover equipped with a plurality of sample inlets and located on the first substrate; iii) a second substrate overlying the adhesive cover; iv) at least one hole penetrating through the first substrate, the adhesive cover, and the second substrate, and formed to extend in the direction intersecting the sample inlet; v) a first electrode that is formed between the first substrate and the adhesive cover, along the circumference of the first substrate; vi) a second electrode that is formed between the first substrate and the adhesive cover to be enveloped by the first electrode; vii) a third electrode that is located between the adhesive cover and the second substrate; and viii) a non-conductive material layer that is located between the first electrode and second electrode and the adhesive cover, while exposing portions of the first electrode and the second electrode. The plurality of sample inlets include a first sample inlet that is formed on one side of the adhesive cover, and a second sample inlet that is formed on the other side of the adhesive cover. The first sample inlet and the second sample inlet are formed at positions that cross each other in an offset manner, and the channel is located between the first sample inlet and the second sample inlet.

The at least one channel may include a plurality of channels, and the channels may be formed to extend parallel to each other. The first electrode may include a first sample measuring unit that is formed between the channels to extend in the direction parallel to the channels. The second electrode may include a second sample measuring unit that is formed apart from the first sample measuring unit by a certain distance and is parallel thereto.

DETAILED DESCRIPTION OF THE EMBODIMENTS

Figure 1:
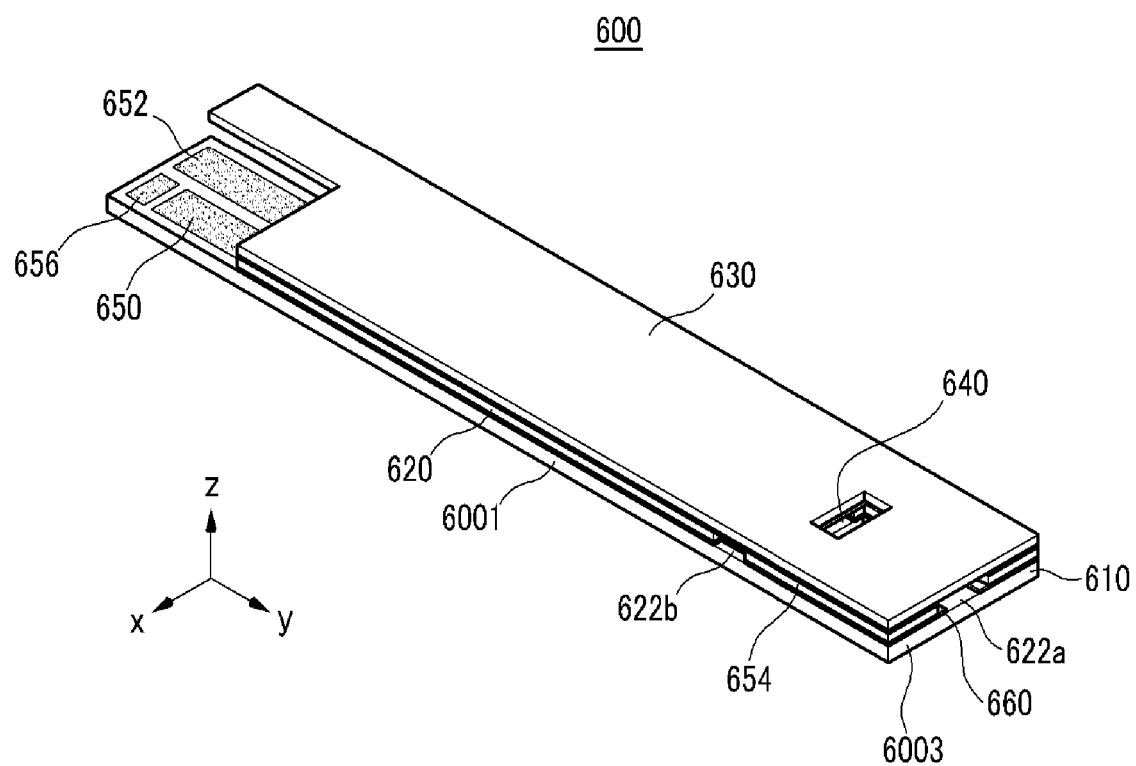
FIG. 1 is a schematic perspective view of a biosensor according to a first embodiment of the present invention.

With reference to the accompanying drawings, embodiments of the present invention will be described in order for those skilled in the art to be able to implement it. As those skilled in the art would realize, the described embodiments may be modified in various different ways, all without departing from the spirit or scope of the present invention. Wherever possible, the same reference numbers will be used throughout the drawings to refer to the same or like parts.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," or "includes" and/or "including", when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath", "below", "lower", "above", "upper", "over", and the like may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein are interpreted accordingly.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

FIG. 1 is a schematic perspective view of the biosensor 600 according to a first embodiment of the present invention.

As shown in FIG. 1, the 600 includes first and second substrates 610 and 630, an adhesive cover 620, a hole 640, a sample guiding layer 660, and first to fourth electrodes 650, 652, 654, and 656. In addition, the biosensor 600 may further include other elements as necessary.

As shown in FIG. 1, the biosensor has a structure that is longitudinally extended along the y-axis direction. Therefore, the left portion of the biosensor 600 can be easily inserted into a display device 700 (shown in FIG. 4, the same hereinafter) along the −y-axis direction. The display device 700 electrically contacts the biosensor 600 to display an amount of materials contained in a sample. Accordingly, a user can easily know the amount of materials contained in the sample. For example, if the sample injected into the biosensor 600 is blood, the display device 700 can display an amount of blood sugar contained in the blood.

As shown in FIG. 1, the first and second substrates 610 and 630 oppose each other. The first and second substrates 610 and 630 may be made of a hard material in order to maintain durability of the biosensor 600. For example, the first and second substrates 610 and 630 may be made of plastic, polyester, polypropylene, or polycarbonate, or of ceramic, glass, and the like, and a polyethylene terephthalate (PET) film based on polyester can be preferably used. The biosensor 600 includes a long edge 6001 and a short edge 6003. The long edge 6001 and the short edge 6003 share a corner of the biosensor 600 and neighbor each other.

The first to fourth electrodes 650, 652, 654, and 656 may be formed in the form of a paste or a plate, using various electrode materials including gold, platinum, silver, carbon, tungsten, nickel, copper, and the like, and a carbon paste is preferably used. The first to fourth electrodes 650, 652, 654, and 656 can be patterned on the first or second substrates 610 and 630 using a method such as screen printing, photolithography, adhesion, vapor deposition, and the like, and are formed such that only the measuring site is distinguishable by means of an insulator film or an adhesive. Here, the first, second, and fourth electrodes 650, 652, and 656 may be formed on the first substrate 610, while the third electrode 654 may be formed on the second substrate 630.

If the sample enters into the biosensor 600, the first to third electrodes 650, 652, and 654 react with the sample and transfer flows of electrons. In this case, the first to third electrodes 650, 652, and 654 function as an operating electrode, a counter electrode, or a recognition electrode. That is, the first electrode 650 functions as the operating electrode, the second electrode 652 functions as the recognition electrode, and the third electrode 654 functions as the counter electrode.

The adhesive cover 620 is located between the first and third electrodes 650 and 654 to electrically insulate them from each other. The adhesive cover 620 may attach the first electrode 650 to the third electrode 654. Adhesive applied on tape that forms the adhesive cover 620 may employ acrylics, urethanes, epoxies, rubber preparations, polyvinyl ether, or silicones, and the film base material may be a PET film.

As shown in FIG. 1, the first, second, and fourth electrodes 650, 652, and 656 are exposed outside toward a +z-axis direction. Here, the fourth electrode 656 is completely exposed to the outside while the first and second electrodes 650 and 652 are partially exposed to the outside. In addition, although not shown in FIG. 1, the third electrode 654 is partially exposed to the outside toward the −z-axis direction. Therefore, the first to fourth electrodes 650, 652, 654, and 656 can be electrically connected to the display device 700 into which the biosensor 600 is inserted.

As shown in FIG. 1, the sample guiding layer 660 has two sample inlets 622a and 622b. The two sample inlets 622a and 622b include first and second sample inlets 622a and 622b. The first sample inlet 622a is formed to correspond to the short edge 6103 of the first substrate 610 while the second sample inlet 622b is formed to correspond to the long edge 6101 of the first substrate 610. Since the biosensor 600 has the two sample inlets 622a and 622b, the biosensor 600 can be used two times by using each of the sample inlets 622a and 622b.

As shown in FIG. 1, since the biosensor 600 includes a hole 640, air in the biosensor 600 can be ventilated to the outside through the hole 640. Therefore, the samples injected into the biosensor 600 through the sample inlets 622a and 622b ventilate the air in the biosensor 600 through the hole 640 while they easily enter therein. Therefore, the material contained in the sample can be measured by using the first to third electrodes 650, 652, and 654 contacting the sample.

Figure 2:
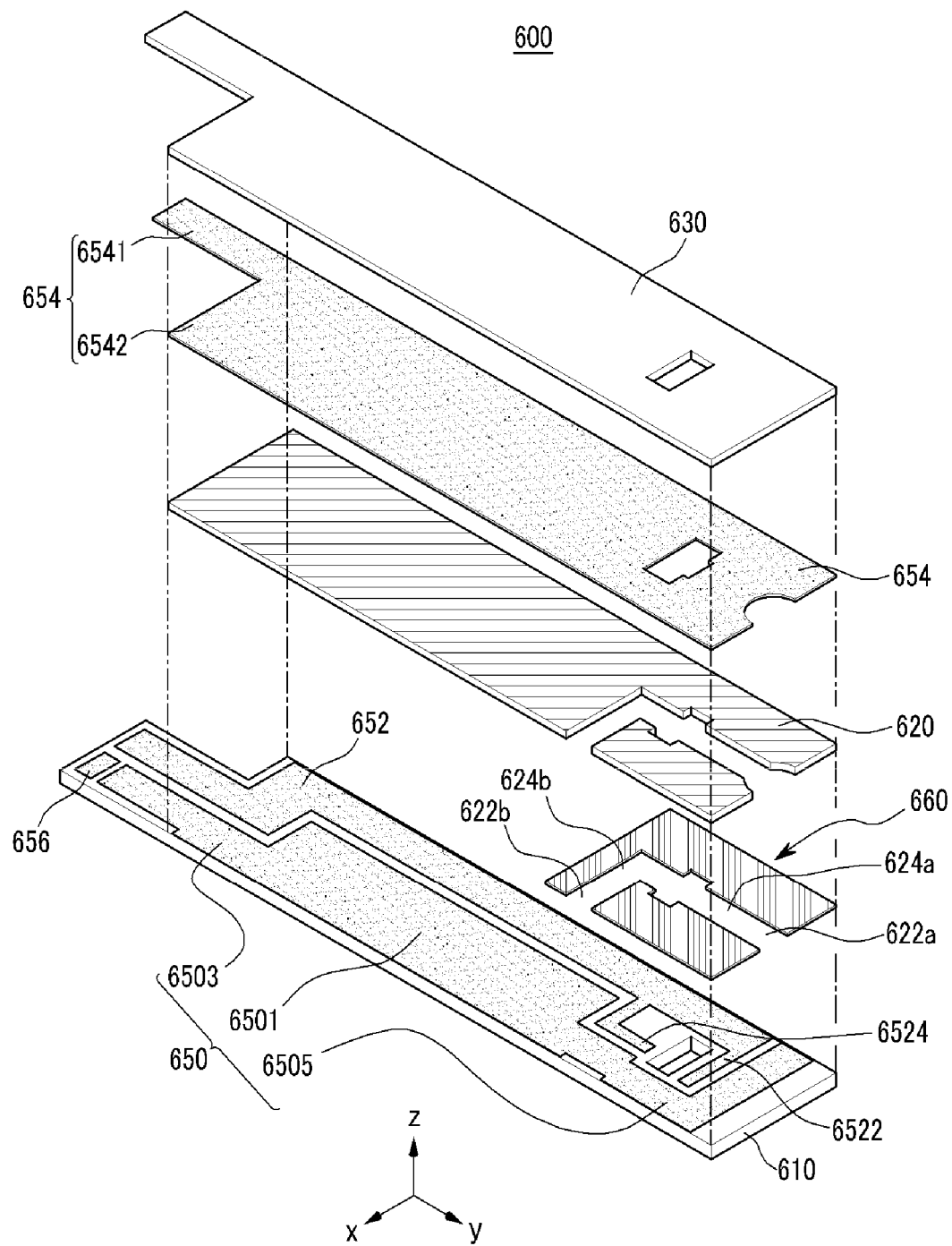
FIG. 2 is a schematic exploded view of the biosensor of FIG. 1.

FIG. 2 schematically shows an exploded state of the biosensor 600 of FIG. 1.

As shown in FIG. 2, the first electrode 650 includes a first body portion 6501, a first connecting portion 6503, and a sample contacting portion 6505. The first body portion 6501 is connected to the first connecting portion 6503 and the sample contacting portion 6505. The first connecting portion 6503 neighbors the fourth electrode 656 and is extended along the −y-axis direction, that is, a direction along which the biosensor 600 is inserted into the display device 700. The first connecting portion 6503 is electrically connected to the display device 700. The sample contacting portion 6505 contacts the sample and then generates an electric signal.

As shown in FIG. 2, the second electrode 652 includes two branched portions 6522 and 6524. The two branched portions 6522 and 6524 include first and second branched portions 6522 and 6524. The first branched portion 6522 is extended along the x-axis direction while the second branched portion 6524 is extended along the y-axis direction. The first and second branched portions 522 and 6524 are spaced apart from the sample contacting portion 6505.

The samples having entered through the sample inlets 622a and 622b consequently contact the sample contacting portion 6505 and the branched portions 6522 and 6524. Therefore, the first to third electrodes 650, 652, and 654 are electrically connected to each other by an electrolyte in the sample. In this case, the second electrode 652 functions as a ground electrode. The material included in the sample is measured by a voltage difference between the first and third electrodes 650 and 654.

As shown in FIG. 2, the sample guiding layer 660 further includes sample guiding channels 624a and 624b. The sample guiding channels 624a and 624b include first and second sample guiding channels 624a and 624b. The first sample guiding channel 624a connects the first sample inlet 622a to the hole 640 while the second sample guiding channel 624b connects the second sample inlet 622b to the hole 640.

Although not shown in FIG. 2, a mediator is located in the first and second sample guiding channels 624a and 624b to react with the sample. The mediator includes an enzyme, an electron transfer medium, and a dispersion stabilizer. In addition, the mediator may further include a surfactant or a phase transfer catalyst.

Here, the enzyme reacts with the material contained in the sample. One or more enzymes can be used depending on the target material to be measured, namely glucose, lactate, alcohol, cholesterol, creatinine, protein, amino acids, environmental materials, or industrial materials. For example, the enzyme may be a glucose oxidase or a glucose dehydrogenase for the purpose of measuring glucose, or an alcohol oxidase or an alcohol dehydrogenase for the purpose of measuring alcohol, PQQ, or NAD/NADH.

The electron transfer medium transfers electrons generated from the enzyme. When the electron transfer medium is used, the formal potential is reduced as compared with the case of using oxygen, and thereby the effect of obstructing species is attenuated and more accurate results can be obtained. As for the electron transfer medium, organic or inorganic compounds including ferrocene, quinone, cobalt, nickel, ruthenium, a ferricyan compound, rhodium, palladium, osmium, iridium, platinum, derivatives containing these, and transition metals can be used. Preferably, hexaammineruthenium(III) chloride is used.

The dispersion stabilizer disperses and stabilizes the enzyme and the electron transfer medium. As for the dispersion stabilizer, polyvinyl alcohol, polyethylene oxide, polyethylene glycol, carboxymethyl cellulose, hydroxymethyl cellulose, 2-hydroxyethyl cellulose, hydroxypropyl cellulose, microcrystalline cellulose, polyvinylpyrrolidone, polyvinylidene fluoride, polymethylmethacrylate, styrene butyl rubber, and the like can be used. Preferably, carboxymethyl cellulose and microcrystalline cellulose are used.

The surfactant is used to confer an improved ability for homogeneous dispersion and solubility to the mediator and to improve the reaction rate. The surfactant simultaneously carries a non-polar terminal group (hydrophobic or lipophilic) and a polar terminal group (hydrophilic or water-soluble) within the same molecule. Also, with regard to the surfactant, a terminal group having affinity for organic substances envelops an organic substance that has no affinity for water, and a polar terminal group oriented outward imparts solubility to the molecule.

The surfactants have properties such as detergency, emulsifiability, dispersibility, and the like. Thus, they can be widely used detergents, emulsifying agents, lubricants, disinfectants, dispersants, and the like, according to their properties. For the purpose of functional improvement, chemical agents and auxiliary agents can be used together with the surfactants.

The surfactant may include at least one of anionic surfactants, cationic surfactants, amphoteric surfactants, and nonionic surfactants. The anionic surfactant ionizes in an aqueous solution to have an anion as the main body of the active agent. The anionic surfactant may be exemplified by a soap, an alkylbenzene sulfonate, or the like. The cationic surfactant ionizes to become a cation. The cationic surfactant may be exemplified by a higher amine halide, a quaternary ammonium salt, an alkylpyridinium salt, and the like. The amphoteric surfactant can ionize to become either a cation or an anion. The amphoteric surfactant may be exemplified by an amino acid and the like. The nonionic surfactant does not ionize. The nonionic surfactant may be exemplified by polyethylene glycols and the like.

The phase transfer catalyst enhances the reaction rate of the mediator and allows low-temperature applications, while it is still effective in reactions involving organic compounds. The phase transfer catalyst is used in the syntheses of inorganic substances that are not soluble in organic solvents, and of organic compounds, and can be usefully used since the phase transfer reaction between water and a solvent occurs homogeneously at normal temperature and normal pressure in an open system. The catalyst can also be used effectively in a liquid-liquid heterogeneous system. In addition, since the fluidity improved by phase transfer is less affected by the changes of the blood type, electromigration can be improved and preserved. For such a phase transfer catalyst, reagents based on phosphonium, crown ether, ammonium, polyethylene glycol, and the like may be used.

Furthermore, the mediator may further include glucose oxidase, hexaammineruthenium(III) chloride, carboxymethyl cellulose, microcrystalline cellulose, tricaprylmethyl ammonium chloride, t-octylphenoxypolyethoxyethanol, or a soap as an auxiliary agent. An amount of the auxiliary agent is in a range from 0.01 wt % to 20 wt %. For example, 0.01 to 20% of a detergent that is a soap, a cationic detergent, and a free fatty acid ($C_{6-20}$) can be added to the mediator. A soap molecule refers to a product having amphotericity (polar and non-polar moieties), which is obtained by subjecting nonionic surfactants such as aliphatic alcohols, acids, amidephenols, alkylphenols, and oxides thereof to an interspecies reaction or a homogeneous reaction. A cationic detergent may be an ammonium compound such as an alkylmethylammonium halide. A free fatty acid ($C_{6-20}$) functions as a protein adsorption preventing agent and as a solubility enhancer.

As shown in FIG. 2, the first and second sample guiding channels 624a and 624b are connected to both sides of the hole 640 opposite to each other. That is, the first and second sample guiding channels 624a and 624b are connected to both sides of the hole 640 opposite to each other along the y-axis direction. Therefore, the biosensor 600 can be used two times by cutting the hole 640.

As shown in FIG. 2, the first branched portion 6522 is located to be closer to the hole 640 than the sample contacting portion 6505 along the first sample guiding channel 624a. In addition, the second branched portion 6524 is located to be closer to the hole 640 than the sample contacting portion 6505 along the second sample guiding channel 624b. Therefore, the samples entering into each of the sample guiding channels 624a and 624b through the sample inlets 622a and 622b can consequently contact the sample contacting portion 6505 and the branched portions 6522 and 6524 while ventilating air existing in the sample guiding channels 624a and 624b toward the hole 640.

The sample guiding layer 660 has a suitable thickness. Therefore, an amount of the samples entering into the biosensor 600 through the sample inlets 622a and 622b can be suitably controlled. Since a voltage difference between the first and third electrodes 650 and 654 is changed to be dependent on an amount of the sample, the amount of the sample is suitably controlled by controlling the thickness of the sample guiding layer 660.

As shown in FIG. 2, the adhesive cover 620 attaches the first and second substrates 610 and 630 to each other. The first, second, and fourth electrodes 650, 652, and 656 are formed on the first substrate 610, while the third electrode 654 is formed on the second substrate 630. Therefore, a short circuit of the electrodes can be prevented by using an insulating material for manufacturing the adhesive cover 620.

The third electrode 654 includes a second body portion 6542 and a second connecting portion that is connected to the second body portion. The second connecting portion 6541 extended along the y-axis direction. Since the second connecting portion 6541 is exposed to the outside toward a direction opposite to a direction of the first connecting portion 6503 of the first electrode 650, that is, the −z-axis direction, it can be electrically connected to the display device 700 into which the biosensor 600 is inserted.

Figure 3:
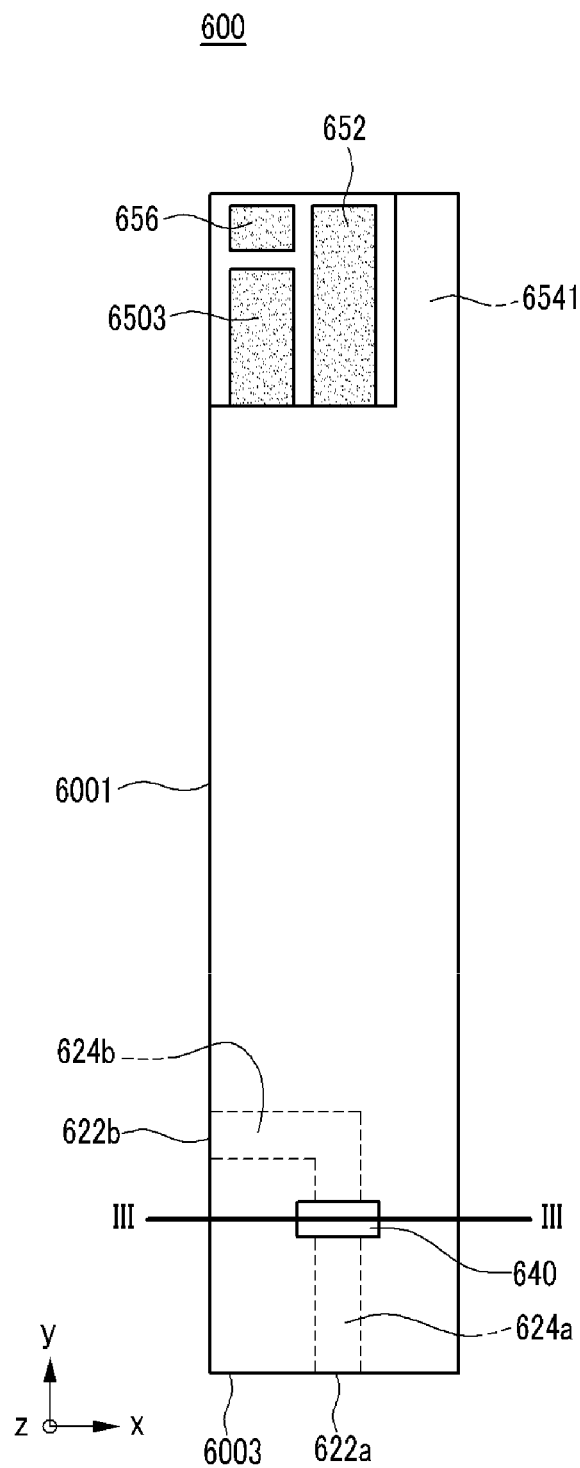
FIG. 3 is a plan view of the biosensor of FIG. 1.

FIG. 3 is a plan view of the biosensor 600 of FIG. 1. FIG. 3 schematically shows a state in which the biosensor 600 of FIG. 1 is cut to be used.

As shown in FIG. 3, the biosensor 600 can be used two times by cutting the biosensor 600 along a line III-III extended in the x-axis direction, which passes through the hole 640. A method for using the biosensor 600 is explained as follows.

First, a sample is injected into the first sample inlet 622a formed at a short edge 6003 of the biosensor 600. For example, after blood is drawn from a finger by piercing it, the finger is contacted with the first sample inlet 622a. When the biosensor 600 is used, it is more convenient to contact the finger with the short edge 6003 of the biosensor 600 than the long edge 6001 thereof. In this case, the blood enters into the biosensor 600 through the first sample inlet 622a and flows through the first sample guiding layer 624a denoted by a dotted line. The air existing in the first sample guiding layer 624a is pressed by the blood and is then ventilated toward the hole 640.

As described above, since the first sample guiding layer 624a meets with the first electrode 650 (shown in FIG. 2, the same hereinafter), the second electrode 652, and the third electrode 654 (shown in FIG. 2, the same hereinafter), the first to third electrodes 650, 652, and 654 are electrically connected to each other, and thereby the material contained in the sample can be measured.

Next, the biosensor 600 is cut along the line III-III. The biosensor 600 can be cut by using a cutter, scissors, or a knife. A cut lower portion of the biosensor 600 is discarded. When the biosensor 600 is reused, the finger is contacted with the second sample inlet 622b after blood is drawn from the finger. In this case, the blood enters into the biosensor 600 through the second sample inlet 622b and flows through the second sample guiding layer 624b denoted by a dotted line. The air existing in the second sample guiding layer 624b is pressed by the blood and is then ventilated toward the hole 640.

As described above, since the second sample guiding layer 624b meets with the first electrode 650, the second electrode 652, and the third electrode 654, the first to third electrodes 650, 652, and 654 are electrically connected to each other, and thereby the material contained in the sample can be measured.

As shown in FIG. 3, the second sample guiding layer 624b is bent. That is, the second sample inlet 622b formed at a long edge 6001 of the biosensor 600 is connected to the hole 640 and the second sample guiding layer 624b to ventilate the air existing in the biosensor 600 during injection of the sample. Since a structure of the electrode should be simple to meet the second sample guiding layer 624b with the first to third electrodes 650, 652, and 654, the second sample guiding layer 624b can be formed to be bent. Particularly, since the biosensor 600 is cut to be reused, the second sample inlet 622b should be located to be higher than the line III-III. Therefore, the second sample inlet 622b is located to be closer to the fourth electrode 656 than the hole 640.

As shown in FIG. 3, the first connecting portion 6503 of the first electrode 650, the second electrode 652, and the second connecting portion 6541 of the third electrode 654 are located side by side along the x-axis direction. Here, the second electrode 652 is located between the first connecting portion 6503 of the first electrode 650 and the second connecting portion 6541 of the third electrode 654. The first connecting portion 6503 of the first electrode 650 and the second connecting portion 6541 of the third electrode 654 are located in symmetrical positions based on the second electrode 652 along a direction perpendicularly crossing an inserting direction of the biosensor 600 into the display device 700, that is, the x-axis direction. Therefore, it is easily determined whether the biosensor 600 is correctly inserted into the display device 700. This will be explained in detail with reference to FIGS. 4 and 5 below.

Figure 4:
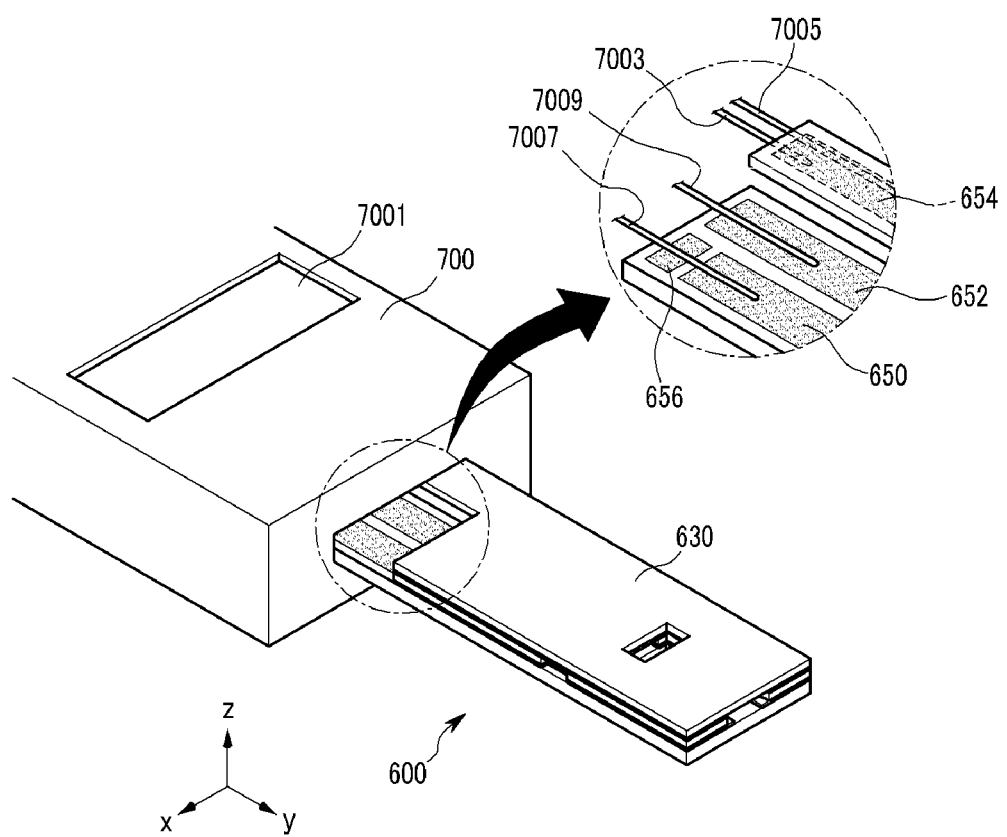
FIG. 4 is a schematic view showing a state in which the biosensor of FIG. 1 is correctly inserted into a display device.

FIG. 4 shows a state in which the biosensor 600 is correctly inserted into the display device 700. An enlarged circle of FIG. 4 shows a magnified end portion of the biosensor 600 inserted into the display device 700.

As shown in FIG. 4, the display device 700 includes a display window 7001. Therefore, when the biosensor 600 is correctly inserted into the display device 700 along the −y-axis direction, the measurement amount of the material is displayed on the display window 7001. Meanwhile, the display device can make a signal sound in addition to a method of showing a message on the display window 7001.

As shown in the enlarged circle of FIG. 4, the display device 700 includes first to fourth connector pins 7003, 7005, 7007, and 7009. Parts of the first and second connector pins 7003 and 7005 located below the second substrate 630 are denoted by dotted lines for convenience. In addition, the third electrode 654 located below the second substrate 630 is also denoted by a dotted line for convenience.

As shown in the enlarged circle of FIG. 4, the second connector pin 7005 is extended to be spaced apart from the first connector pin 7003. The second connector pin 7005 has a greater length than that of the first connector pin 7003. Both of the first and second connector pins 7003 and 7005 electrically contact the third electrode 654.

A circuit of the display device 700 is structured to operate only when both of the first and second connector pins 7003 and 7005 connect to the third electrode 654. Since a circuit structure of the display device 700 can be easily understood by the skilled art, a detailed description thereof is omitted.

Meanwhile, the third connector pin 7007 is connected to the first electrode 650 and thereby transfers an electric signal. Since an end portion of the third connector pin 7007 is conductive, the third connector pin 7007 passing above the fourth electrode 656 is not electrically connected to the fourth electrode 656. An amount of the material is displayed on the display window 7001 of the display device 700 depending on the voltage difference between the second and third connector pins 7705 and 7707. Meanwhile, the fourth connector pin 7009 is electrically connected to the second electrode 652 to transfer a timing signal.

It is necessary to prevent the biosensor 600 from being misused by a regulation of the food and drug administration (FDA). Therefore, in an embodiment of the present invention, the display device 700 displays an error message when the biosensor 600 is incorrectly inserted into the display device 700. This will be explained in detail below with reference to FIG. 5.

Figure 5:
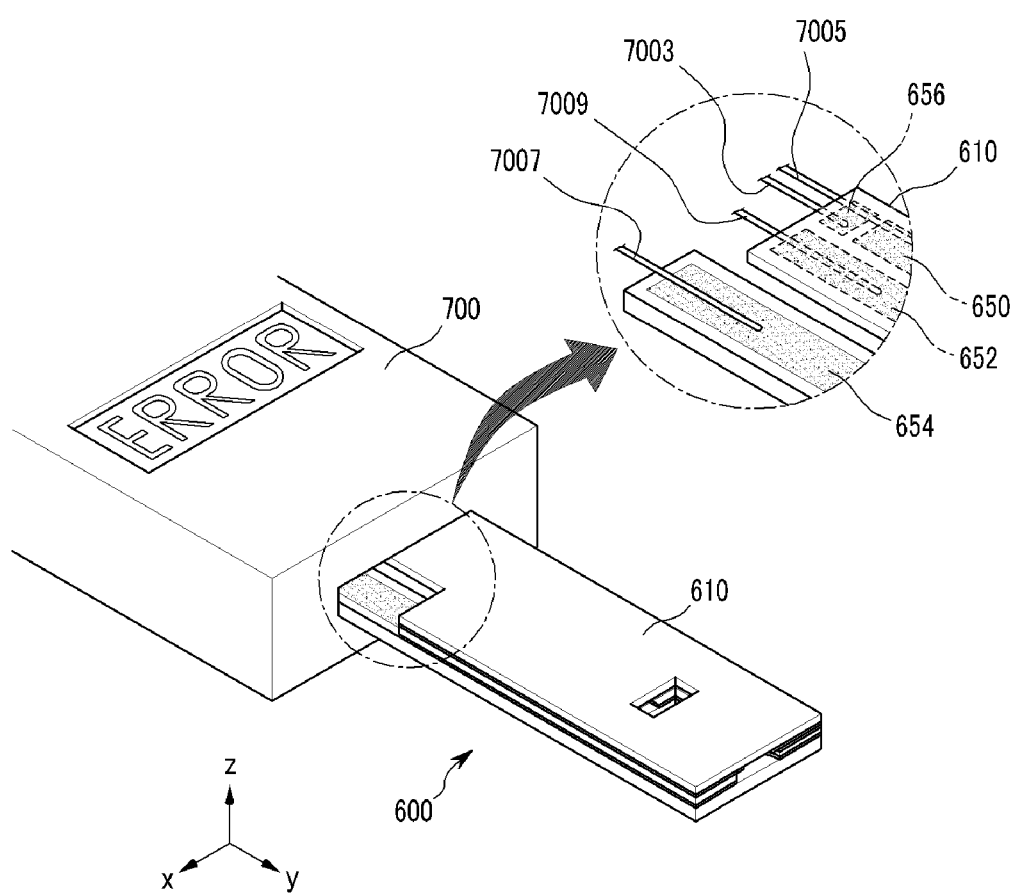
FIG. 5 is a schematic view showing a state in which the biosensor of FIG. 1 is incorrectly inserted into a display device.

FIG. 5 schematically shows a state in which the biosensor 600 is incorrectly inserted into the display device 700. An enlarged circle of FIG. 5 shows a magnified end portion of the biosensor 600 inserted into the display device 700. Since the biosensor 600 and the display device 700 of FIG. 5 are the same as those of FIG. 4 except that the biosensor 600 is overturned, like elements are referred to by like reference numerals and detailed descriptions thereof are omitted.

As illustrated in FIG. 5, when the overturned biosensor 600 is inserted into the display device 700, the fourth electrode 656 is located to be closer to the display device 700 than the first electrode 650. Since the length of the first connector pin 7003 is different from that of the second connector pin 7005, the first connector pin 7003 is electrically connected to the fourth electrode 656 while the second connector pin 7005 is electrically connected to the first electrode 650. Since an end portion of the second connector pin 7005 is conductive, the second connector pin 7005 passing above the fourth electrode 650 is electrically insulated from the fourth electrode 650.

Here, since the fourth electrode 656 is not electrically connected to the first electrode 650, the first connector pin 7003 cannot transfer an electric signal to the display device 700. Meanwhile, the second connector pin 7005 is electrically connected to the fourth electrode 650 and thereby transfers an electric signal to the display device 700. Here, the display device 700 has a circuit structure to operate only when electric signals enter from the first and second connector pins 7003 and 7005, and thereby the display device 700 does not operate and an error message is displayed on the display window 7001. On the contrary, the display device 700 can emit an error message by making a warning sound.

Figure 6:
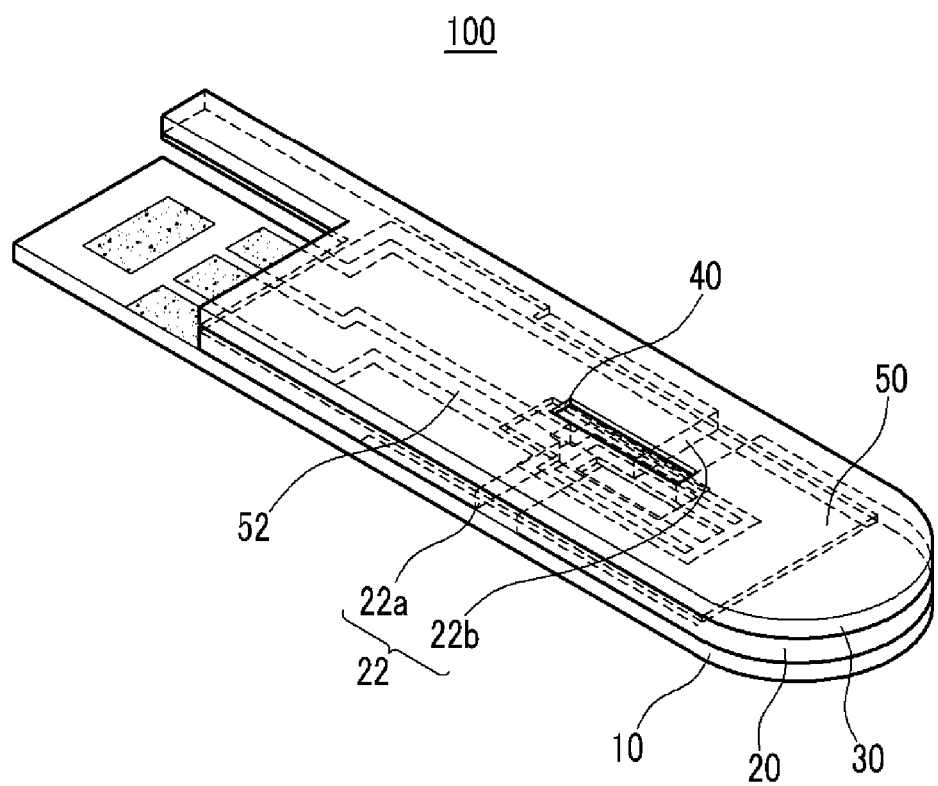
FIG. 6 is a perspective view of a biosensor according to a second embodiment of the present invention.

FIG. 6 is a perspective view of a biosensor 100 according to a second embodiment of the present invention. Since the structure of the biosensor 100 according to the second embodiment of the present invention is similar to that of the biosensor 600 of FIG. 1, detailed descriptions of the same parts are omitted.

As shown in FIG. 6, the biosensor 100 includes a first substrate 10, a first electrode 50 and a second electrode 52 formed on the first substrate 10, an adhesive cover 20 equipped with a sample inlet 22 and located on the first substrate 10, and a second substrate 30 overlying the adhesive cover 20. Furthermore, the biosensor 100 includes a hole 40 that is formed to penetrate through the first substrate 10, the adhesive cover 20, and the second substrate 30. The sample inlet 22 includes a first sample inlet 22a that is provided on one side of the biosensor 100 and a second sample inlet 22b that is provided on the other side, and the hole 40 is formed in the direction intersecting the first sample inlet 22a and the second sample inlet 22b. The hole 40 is located between the first sample inlet 22a and the second sample inlet 22b.

Figure 7:
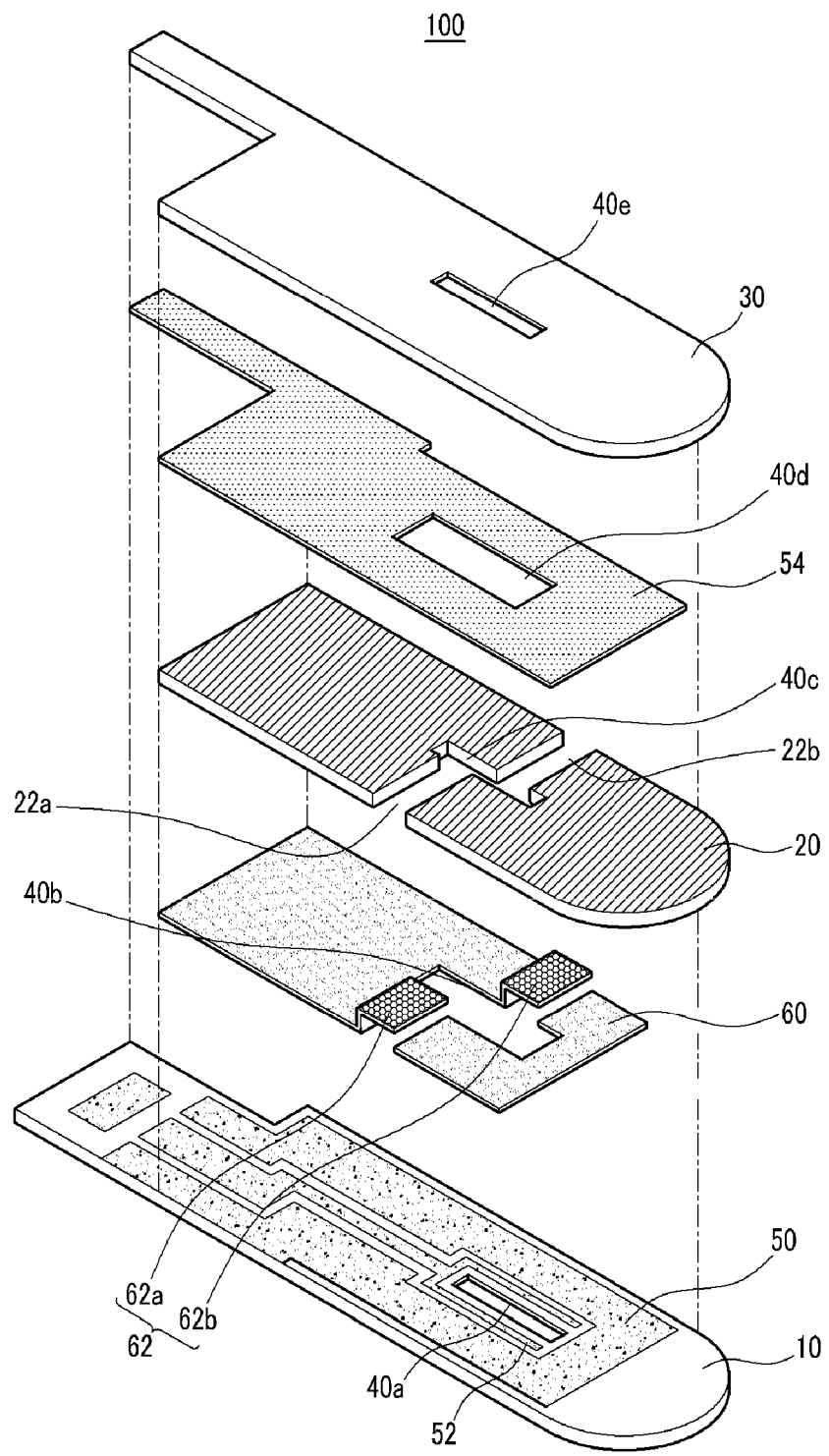
FIG. 7 is an exploded perspective view of the biosensor according to the second embodiment of the present invention.

FIG. 7 is an exploded perspective view of a biosensor 100 according to the second embodiment of the present invention. Hereinafter, each of the constituent elements of the biosensor 100 will be described in more detail with reference to FIG. 7.

As shown in FIG. 7, the biosensor 100 includes a mediator 62 that is introduced on an electrode defined to have a specific site among the electrodes. The mediator 62 includes first and second mediators 62a and 62b. In the second embodiment of the present invention, the mediator 62 is immobilized on a specific portion of the first electrode 50. The mediator 62 contains an enzyme that reacts with a material contained in the sample to be introduced through the sample inlet 22, an electron transfer medium that transfers electrons generated from the enzyme, and a dispersion stabilizer that disperses and stabilizes the enzyme and the electron transfer medium. The components of the mediator 62 are the same as those of the mediator explained in the first embodiment of the present invention.

Hole portions 40a to 40e, which are parts of the hole 40, are formed in the first substrate 10 and the second substrate 30. The first substrate 10 and the second substrate 30 may be formed of a material that is the same as that of the first and second substrates 610 and 630 of the biosensor 600 of FIG. 2.

The adhesive cover 20, which is located between the first substrate 10 and the second substrate 30, forms the sample inlet 22 while adhering the first substrate 10 and the second substrate 30 to each other. Here, a hole portion 40c that is a part of the hole 40 is also formed in the adhesive cover 20. The adhesive cover 20 may be formed from a film-based tape that has an adhesive applied on either side or both sides thereof. The adhesive applied on the tape that forms the adhesive cover 20 may employ acrylics, urethanes, epoxies, rubber preparations, polyvinyl ether, or silicones, and the film base material may be a PET film.

The biosensor 100 further includes a third electrode 54 that is located between the adhesive cover 20 and the second substrate 30. In addition, the first electrode 50 is formed on the first substrate 10 along the circumference of the first substrate 10, and the second electrode 52 is located to be enveloped by the first electrode 50 and is formed to envelop the holes formed in the first substrate 10. These electrodes transfer the flow of electrons generated by a reaction occurring after the introduction of a sample. Here, each of the electrodes acts as an operating electrode, a counter electrode, or a recognition electrode, and if necessary, three or more electrodes may be formed. According to the second embodiment of the present invention, as an example, the first electrode 50 serves as an operating electrode, the second electrode 52 serves as a recognition electrode, and the third electrode 54 serves as a counter electrode. Meanwhile, a hole portion 40d that is a part of the hole 40 is also formed in the third electrode 54.

The first electrode 50, the second electrode 52, and the third electrode 54 may be formed in the form of a paste or a plate, using various electrode materials including gold, platinum, silver, carbon, tungsten, nickel, copper, and the like, and a carbon paste is preferably used. The electrodes 50, 52, and 54 can be patterned on a substrate using a method such as screen printing, photolithography, adhesion, vapor deposition, and the like, and are formed such that only the measuring site is distinguishable by means of an insulator film or an adhesive.

The biosensor 100 further includes a non-conductive material layer 60 between the first electrode 50 and second electrode 52 and the adhesive cover 20, so that only parts of the first electrode 50 and the second electrode 52 are used as the measuring site. A hole portion 40b that is a part of the hole 40 is also formed in the non-conductive material layer 60.

As described above, the hole 40 is formed such that the hole portions 40a to 40e, which are respectively formed at the same positions on the first substrate 10, the non-conductive material layer 60, the adhesive cover 20, the third electrode 54, and the second substrate 30, together penetrate through the biosensor 100 as a whole. Such a hole 40 is formed in the direction intersecting the sample inlet 22. For example, the hole 40 is formed to extend in the direction perpendicular to the first sample inlet 22a and the second sample inlet 22b, which are formed parallel to each other.

As the hole 40 is provided as such, the samples injected through the first sample inlet 22a and the second sample inlet 22b are prevented from flowing into the other sample inlet 22. Thus, by using the different sample inlets 22 separately, the amount of sample can be reduced to half, as compared to the case where the hole 40 is not included. Therefore, the biosensor 100 having a structure as described above can be readily applied to electrochemical biosensors that require small amounts of samples.

According to the second embodiment of the present invention, the first sample inlet 22a and the second sample inlet 22b are located to cross each other in an offset manner. Thus, a measurement is performed when a sample is injected through the second sample inlet 22b, then the portion where the second sample inlet 22b is formed is cut, and another measurement can be performed using the first sample inlet 22a. On the other hand, the shapes of the sample inlets 22 and the hole 40 depicted in FIGS. 6 and 7 are intended only to illustrate the present invention, and the shape, slope, dimensions, and width may be varied in accordance with different conditions.

Figure 8:
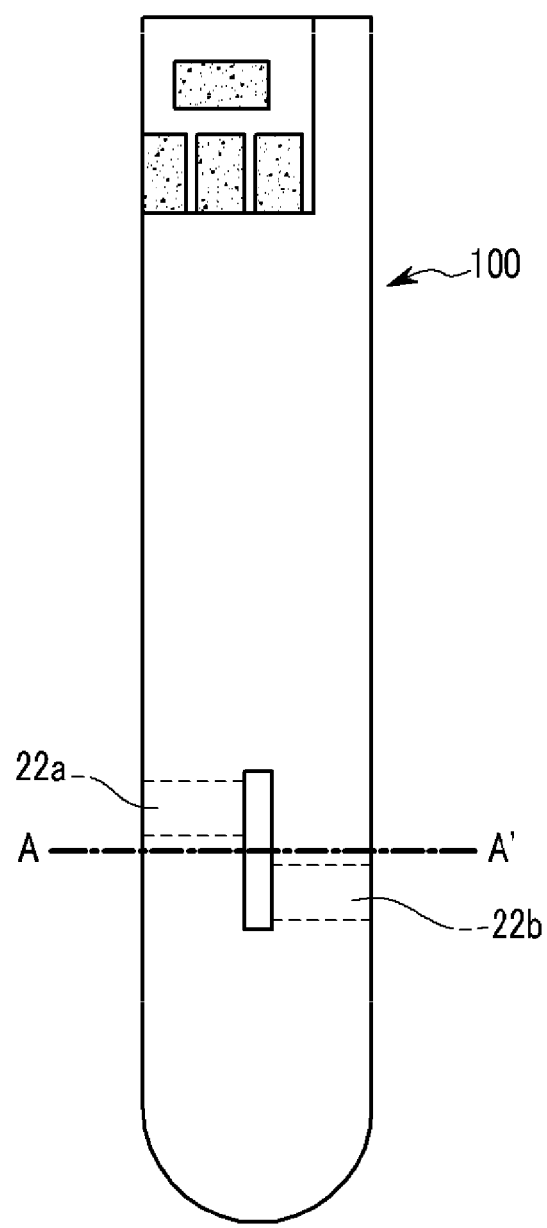
FIGS. 8 and 9 are plan views of the biosensor according to the second embodiment of the present invention.
Figure 9:
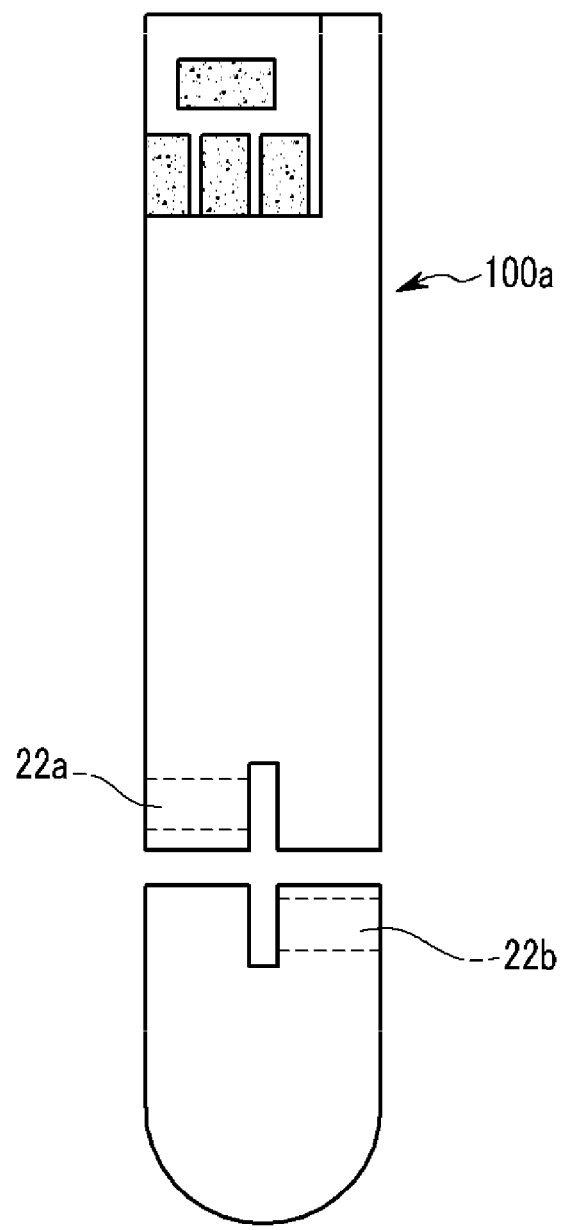

FIGS. 8 and 9 are plan views of the biosensor according to the second embodiment of the present invention, and depict a biosensor 100 before cutting and a biosensor 100a after cutting, respectively. As depicted therein, the biosensor 100 is cut along the line indicated by the line A-A' so that the portion where the second sample inlet 22b is placed is cut off, and the remaining portion where the first sample inlet 22a is placed is reused.

Figure 10:
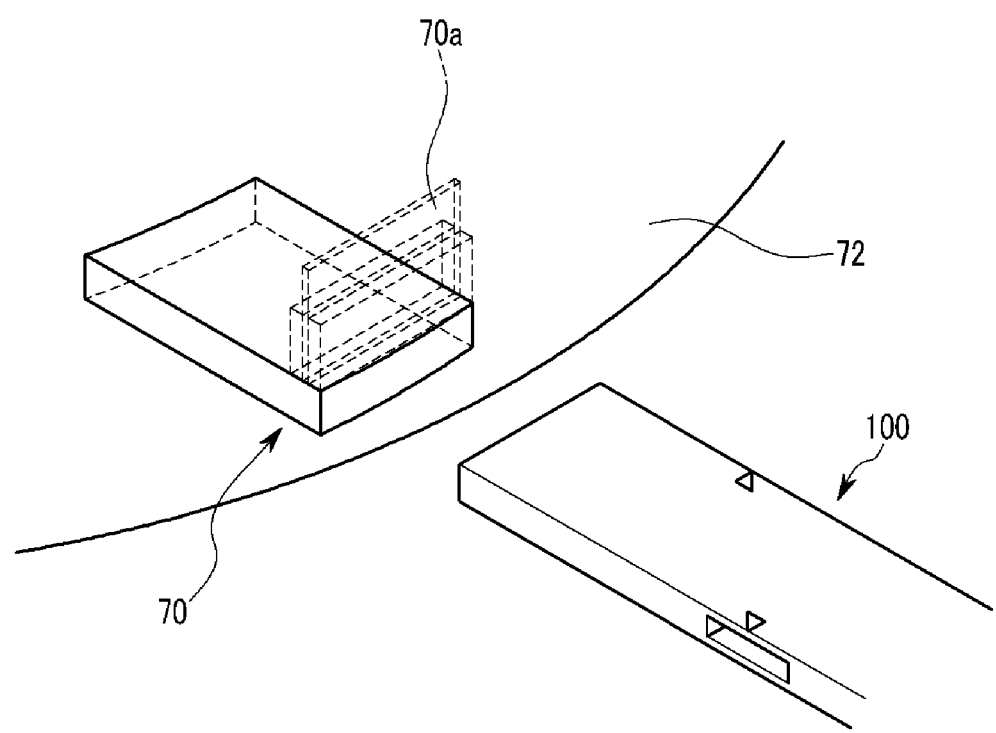
FIGS. 10 to 12 are schematic perspective views showing a method of cutting the biosensor according to the second embodiment of the present invention.
Figure 11:
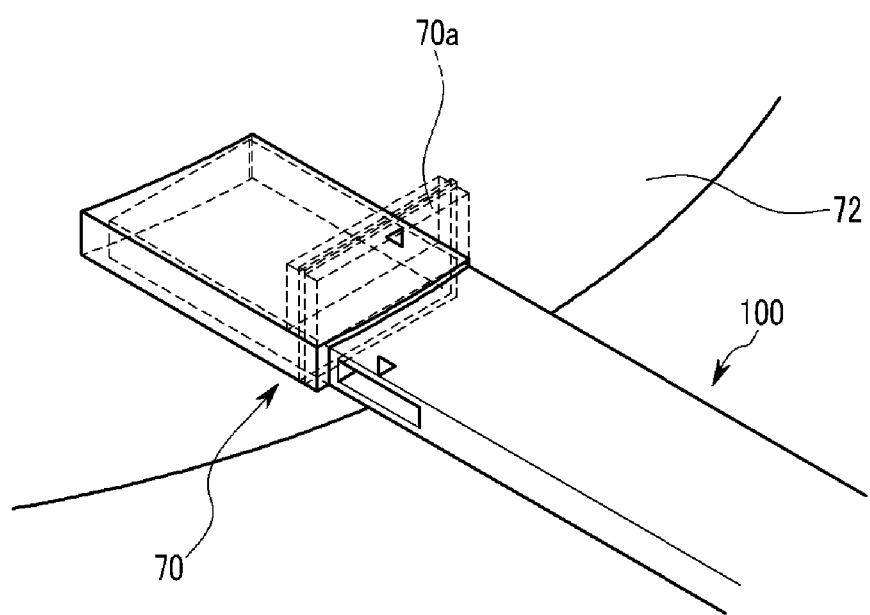
Figure 12:
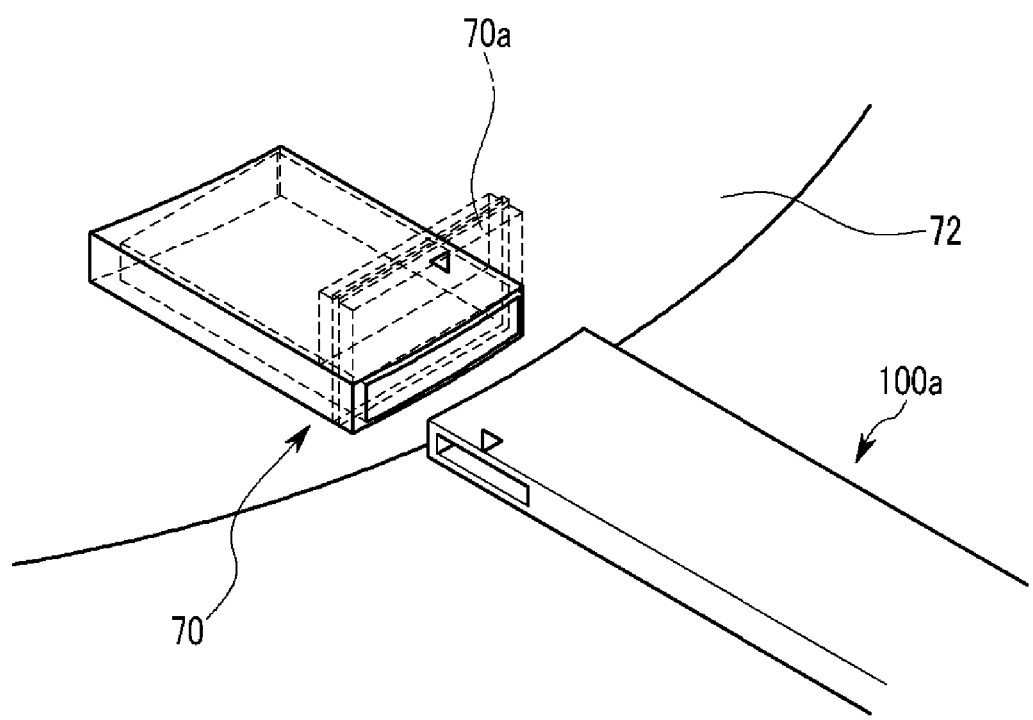

FIGS. 10 to 12 are schematic diagrams sequentially illustrating the process of cutting a biosensor having the above-described structure. As depicted therein, a portion of the biosensor is inserted into a cutting device 70, and a cutter 70a included in the cutting device 70 is used to cut the biosensor 100. Here, the cutting device 70 may be located inside or outside a measurement display device 72, or may be provided separately from the measurement display device 72. FIGS. 10 to 12 illustrate an example in which the cutting device is located inside the measurement display device 72.

Figure 13:
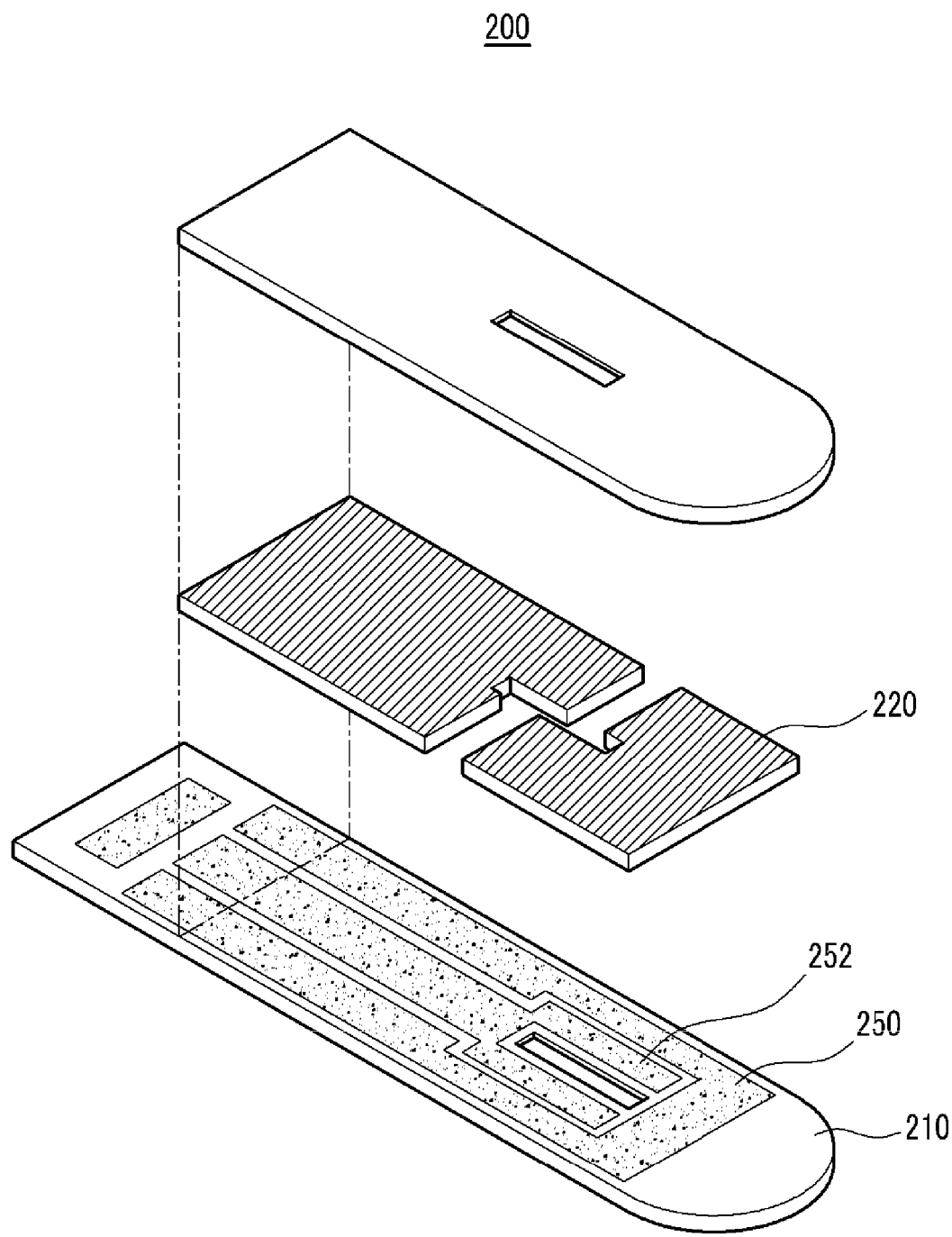
FIG. 13 is an exploded perspective view of a biosensor according to a third exemplary embodiment of the present invention.

FIG. 13 is an exploded perspective view of a biosensor 200 according to a third embodiment of the present invention. As shown in FIG. 13, the biosensor 200 has electrodes formed only between a first substrate 210 and an adhesive cover 220. That is, according to the third embodiment of the present invention, only a first electrode 250 and a second electrode 252 are formed on the first substrate 210 to act as an operating electrode and a counter electrode, respectively. Since the remaining constitution of the third embodiment of the present invention is identical to that of the first embodiment of the present invention, a description thereof will be omitted herein.

Figure 14:
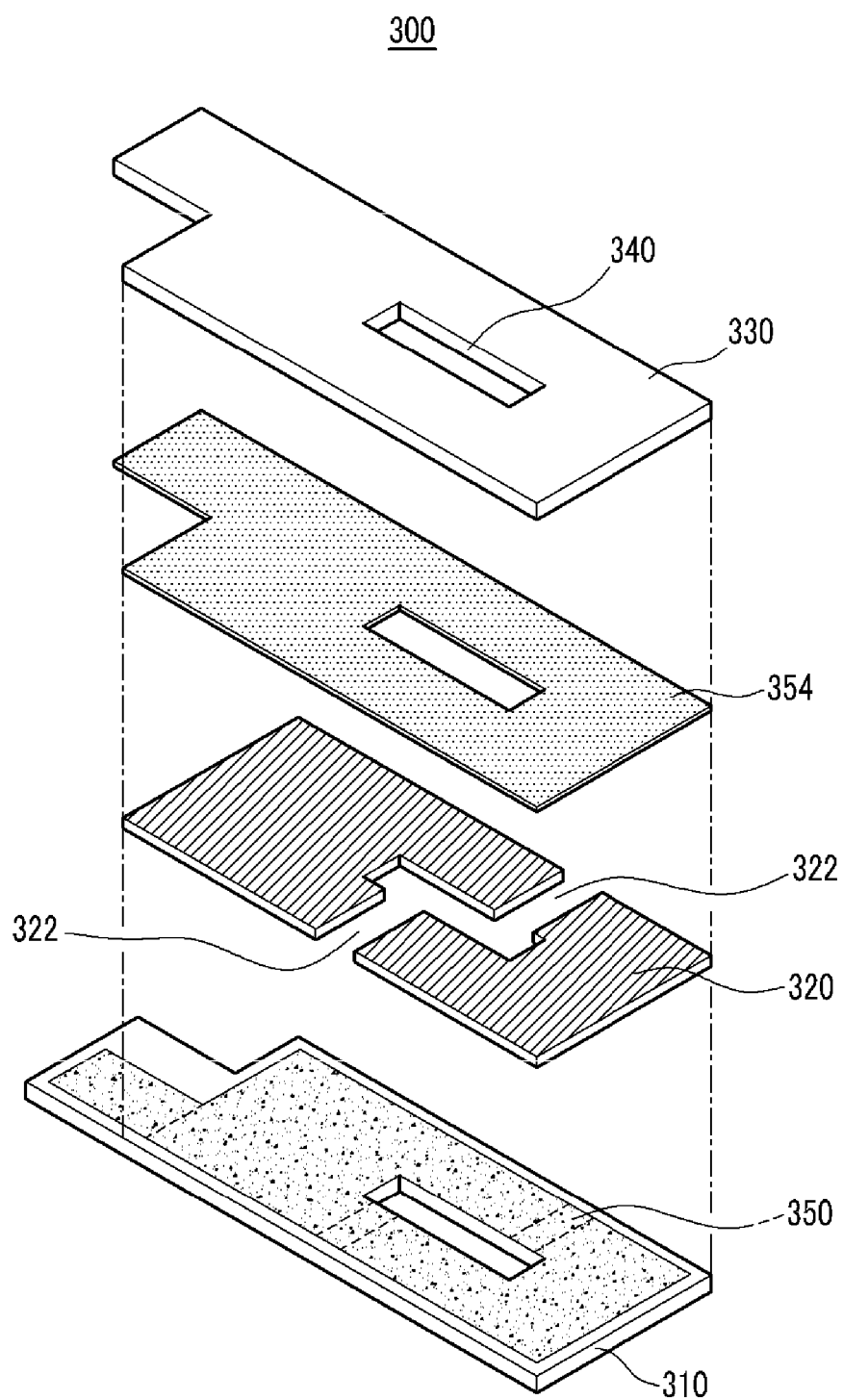
FIG. 14 is an exploded perspective view of a biosensor according to a fourth embodiment of the present invention.

FIG. 14 is an exploded perspective view of a biosensor 300 according to a fourth embodiment of the present invention. As depicted in FIG. 14, in the biosensor 300 according to the fourth embodiment of the present invention, an electrode 350 covering approximately the entire surface of a first substrate 310, excluding a hole 340, is formed on the first substrate 310, and another electrode 354 covering approximately the entire surface of an adhesive cover 320, except the hole 340, is formed between the adhesive cover 320 and a second substrate 330. Here, either one of the two electrodes serves as an operating electrode while the other serves as a counter electrode, thus constituting opposing electrodes.

In this case, even if the width of the electrodes 350 and 354 as a whole is set to 0.5 cm or greater, the width of the channel can be laterally adjusted to allow a sample to be introduced in an amount of only half the conventional amount or less.

Furthermore, different mediators intended for different purposes can be introduced through sample inlets 322 placed on both sides of the biosensor 300, so that two or more different target materials can be detected. The measuring unit sensor manufactured in an arbitrary form according to the fourth embodiment can be directly modified with an enzyme, an antibody, or a molecule-recognition material on the electrode, or can be modified first and then be introduced onto the electrode, or alternatively, membranes containing various mediators can also be introduced. Since the remaining constitution of the fourth embodiment of the present invention is identical to that of the first embodiment of the present invention, a description thereof will be omitted herein.

Figure 15:
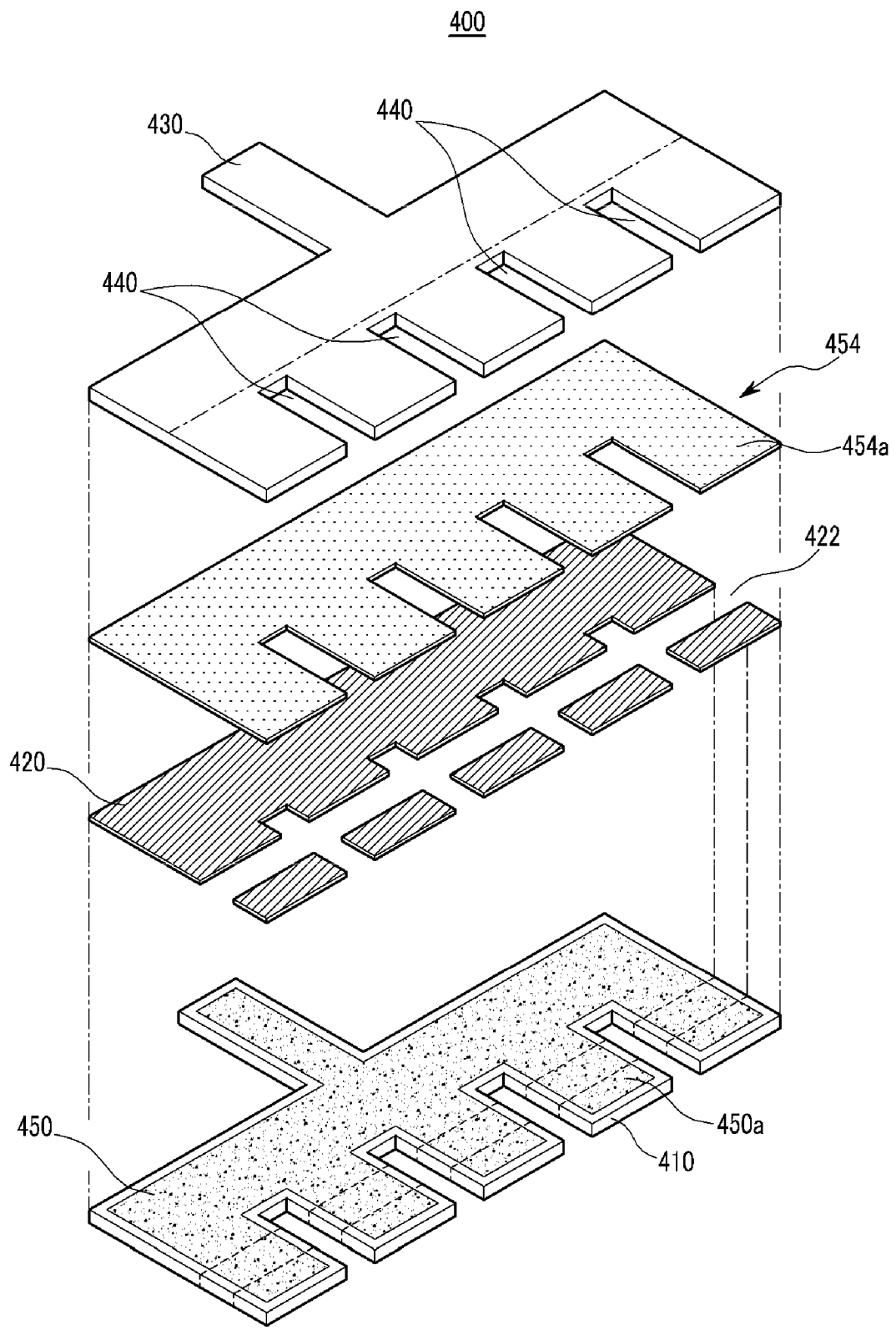
FIG. 15 is an exploded perspective view of a biosensor according to a fifth embodiment of the present invention.

FIG. 15 is an exploded perspective view of a biosensor 400 according to a fifth embodiment of the present invention. As depicted in FIG. 15, the biosensor 400 according to the fifth embodiment of the present invention includes a plurality of holes 440, and the plurality of holes 440 are formed to extend parallel to each other. Thus, a first electrode 450 having a shape with many branches extending out from one stem is located between a first substrate 410 and an adhesive cover 420, and a second electrode 454 having a corresponding shape is located between the adhesive cover 420 and a second substrate 430. Here, the first electrode 450 and the second electrode 454 may serve as an operating electrode and a counter electrode, respectively.

According to the fifth embodiment of the present invention, electrode cells 450a and 454a formed from the first electrode 450 and the second electrode 454 into many branches can be respectively used as measuring cells for samples. In this case, more electrode cells 450a and 454a can be formed in parallel, and the position, path, or shape of sample inlets 422 can be altered, or alternatively the limited portions of the electrode cells 450a and 454a can be adjusted vertically to form gaps therebetween.

Figure 16:
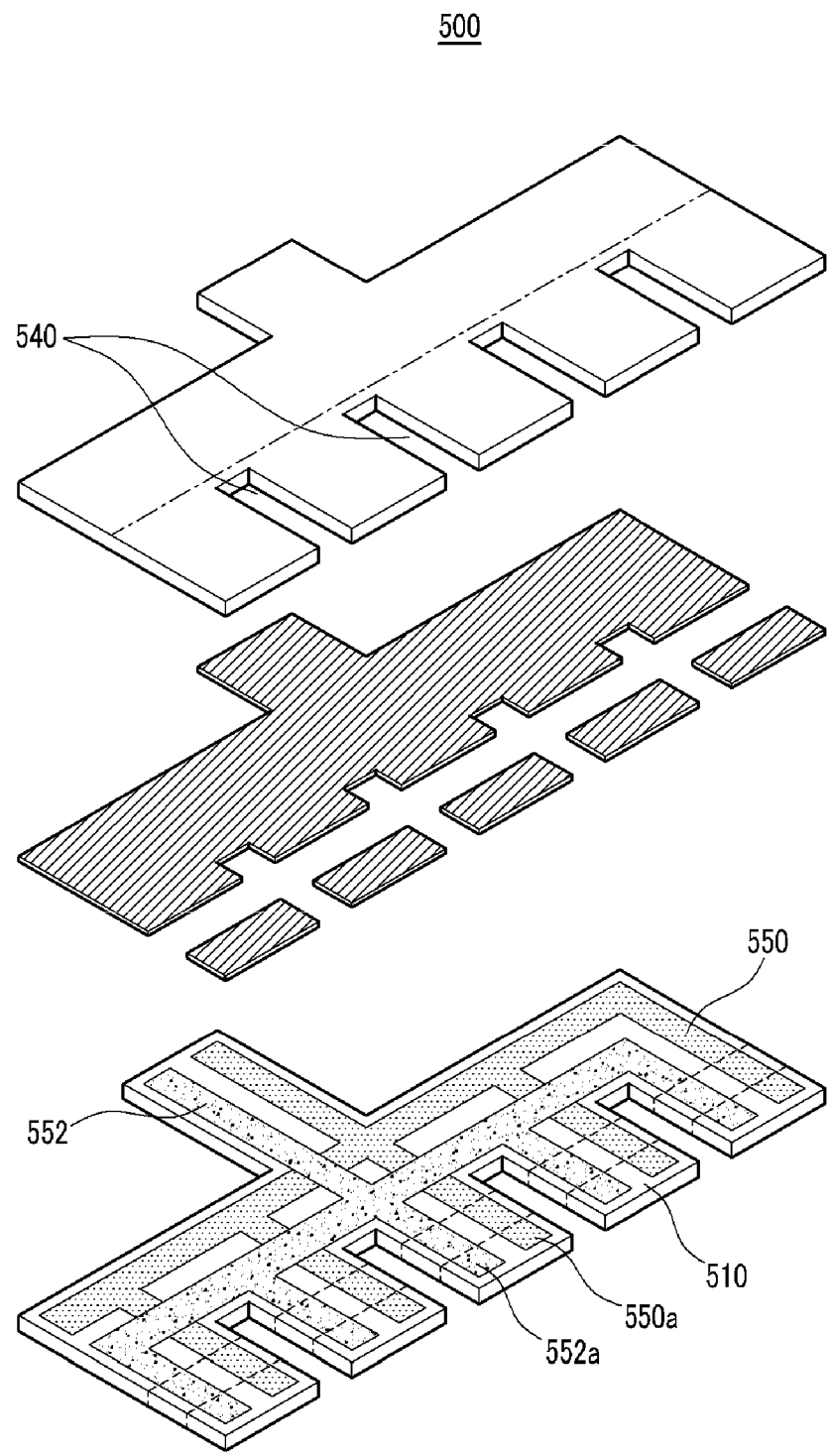
FIG. 16 is an exploded perspective view of a biosensor according to a sixth embodiment of the present invention.

In addition, FIG. 16 is an exploded perspective view of a biosensor 500 according to a sixth embodiment of the present invention. In the biosensor 500 according to the sixth embodiment of the present invention, two electrodes are formed on a first substrate 510. That is, the biosensor 500 of the sixth embodiment of the present invention includes a first electrode 550 that is formed on the first substrate 510, an insulating layer (not shown in the drawing) that is formed on the first electrode 550, and a second electrode 552 that is formed on the insulating layer. Furthermore, the first electrode 550 includes a first sample measuring unit 550a that is formed between holes 540 so as to extend in a direction parallel to the holes 540, and the second electrode 552 includes a second sample measuring unit 552a that is placed apart from the first sample measuring unit 550a by a certain distance and formed in parallel. Thus, the first electrode 550 and the second electrode 552 can serve as an operating electrode and a counter electrode, respectively.

Hereinafter, the present invention will be described in detail with reference to an experimental example. The following experimental example is intended only to illustrate the present invention, and the present invention is not limited thereto.

Experimental Example

A biosensor identical to that of the second exemplary embodiment of the present invention was produced. An operating electrode and a recognition electrode formed of a conducting carbon paste were formed on the first substrate, and a counter electrode was formed simultaneously with electrode connections on the second substrate by a screen printing method. Next, the assembly was dried in a dry oven at 100° C. for 20 minutes. Then, while a specific portion to be used as an electrode cell was left intact, the remaining portion was applied with an insulating paste.

Also, a channel having a size of 0.8×1 mm was formed in the mid-portion of the electrode and the adhesive cover by pressing in a mold that was processed in advance. Subsequently, a mediator was immobilized on the electrode cell, and then, while leaving the contacting portion, the remaining portion was attached to the adhesive cover to form a sample inlet. Next, a co-solution A and a solution B having composition ratios as indicated in Table 1 were prepared.

TABLE 1

| COMPONENT | SOLUTION A (wt %) | SOLUTION B (wt %) |
|---|---|---|
| glucose oxidase | 35 | 38.5 |
| ruthenium (III) hexaamine | 25 | 20.5 |
| carbonylmethyl cellulose | 0.3 | 0.3 |
| microcrystalline cellulose | — | 0.2 |
| Tricaprylmethyl ammonium chloride | — | 0.08 |
| t-Octylphenoxypolyethoxyethanol | 1.5 | 2 |
| Soap | — | 0.5 |

A 100 mM phosphate buffer saline (PBS) at pH 6.5 was prepared. Then, an enzyme (glucose oxidase), an electron transfer medium [ruthenium(III) hexaamine], and carboxymethyl cellulose and 10 mg of t-octylphenoxypolyethoxyethanol as dispersion stabilizers were sequentially added to 1 ml of PBS.

In the solution B, microcrystalline cellulose, tricaprylmethyl ammonium chloride, and a soap were further added.

The prepared composition solutions, solution A and solution B, were applied on the electrode of the first substrate in an amount of 1.5 mg, respectively, and then were dried at 50° C. for 20 minutes to be immobilized thereon. Subsequently, the molded adhesive cover was attached thereon and the second substrate was laid thereupon, and the assembly was pressed.

Figure 17:
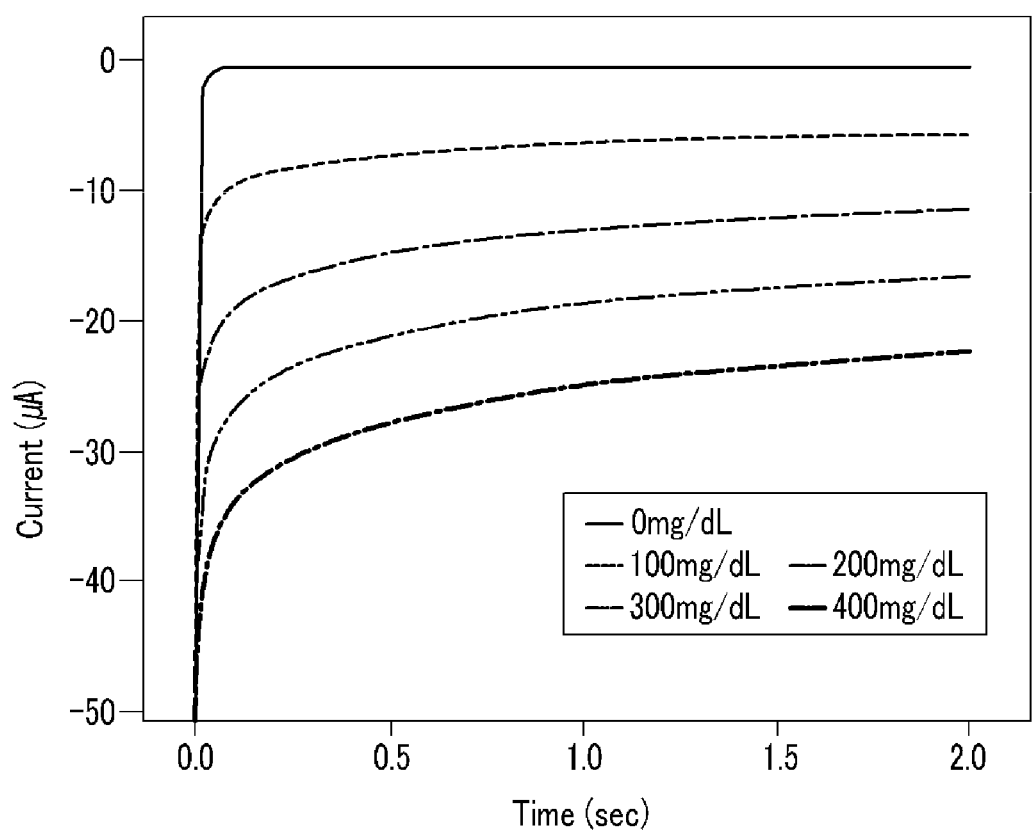
FIG. 17 is a dynamic response curve showing the results of measurements taken in the experimental example of the present invention using a constant voltage and current method.

First, the sensitivity of the biosensor with respect to the constant voltage vs. current method (chronoamperometry) was measured using a glucose standard solution. FIG. 17 is a dynamic response curve obtained when the solution B was immobilized on the electrode and then the electrochemical measuring method according to a constant voltage vs. current method was applied to the biosensor prepared as described above. Here, the measurement range was 0, 100, 200, 300, and 400 mg/dL of the standard glucose solution. After the sample was filled in the sample inlet, the amount of change in the current over time was measured by maintaining the constant voltage at an applied potential of 300 mV. Here, the slope was 0.06 [µA/(mg/dL)], and the linearity was 0.99, thus excellent linear sensitivity was exhibited at each concentration.

Figure 18:
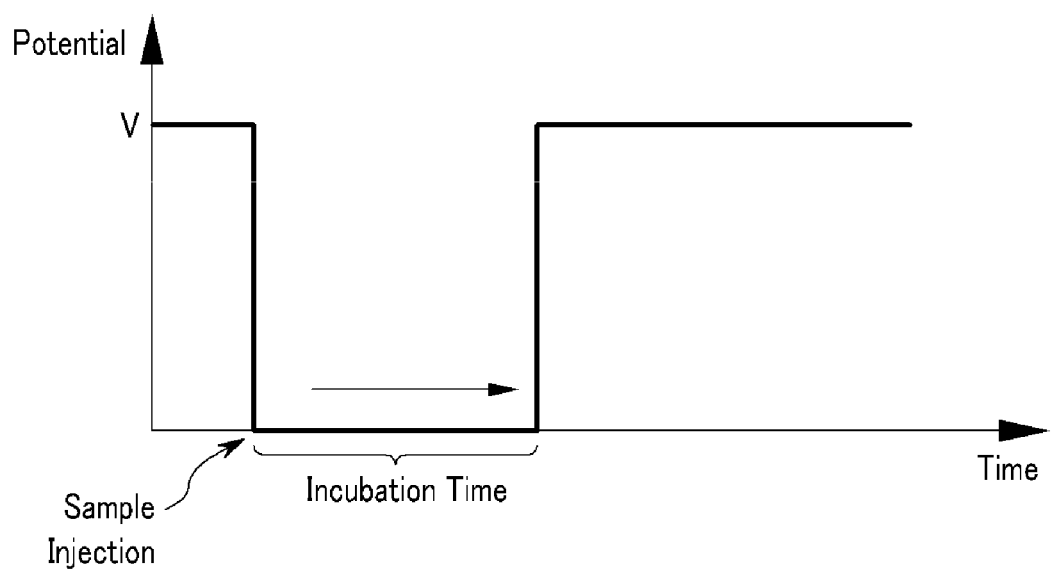
FIG. 18 is a graph showing the principle of the measurement taken in the experimental example of the present invention using a constant voltage and current method.

Next, the sensitivity of the biosensor for a blood sample under optimization of the mediator was measured. Using the biosensor prepared as described above, measurements were taken according to the method of FIG. 18, by varying the glucose concentration and the hematocrit (Hct).

When the blood sample is brought into contact with the sample inlet, the blood sample instantaneously fills the whole channel, and a catalytic reaction involving the following Reaction Scheme 1 takes place.

Glucose+$GO_x$-FAD→Gluconic acid+$GO_x$-$FADH_2$

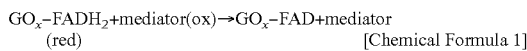

$GO_x$-$FADH_2$+mediator(ox)→$GO_x$-FAD+mediator
(red)                                    [Chemical Formula 1]

In Chemical Formula I, $GO_x$-$FADH_2$ and $GO_x$-FAD respectively represent the reduced state and the oxidized state of flavin adenine dinucleotide (FAD), which is the active site of glucose oxidase ($GO_x$).

When the sample is in contact with the recognition electrode, the voltage between the electrodes is cut off, and an incubation time of 6 seconds occurs. After 6 seconds, a constant voltage of 300 mV was applied through the operating electrode and the counter electrode. Then, the amount of change in the current flow flowing through the electrodes was measured to calculate the glucose concentration.

Figure 19:
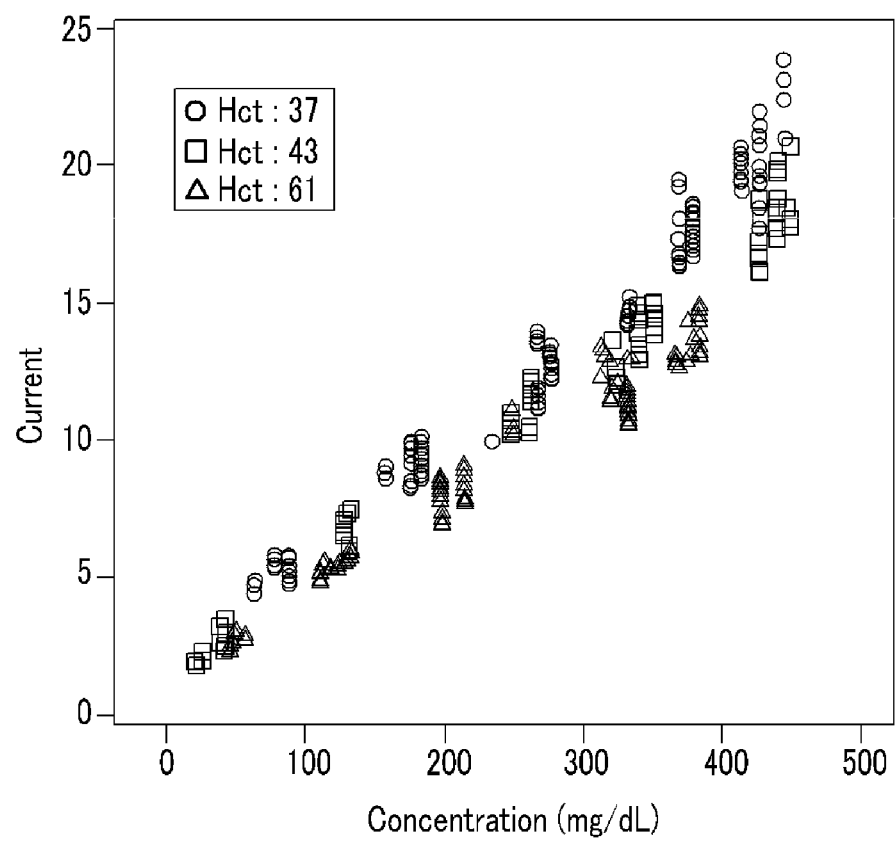
FIG. 19 is a graph showing the results of measurements made by varying the erythrocyte volume and the glucose concentration before compatibilizing the mediator.
Figure 20:
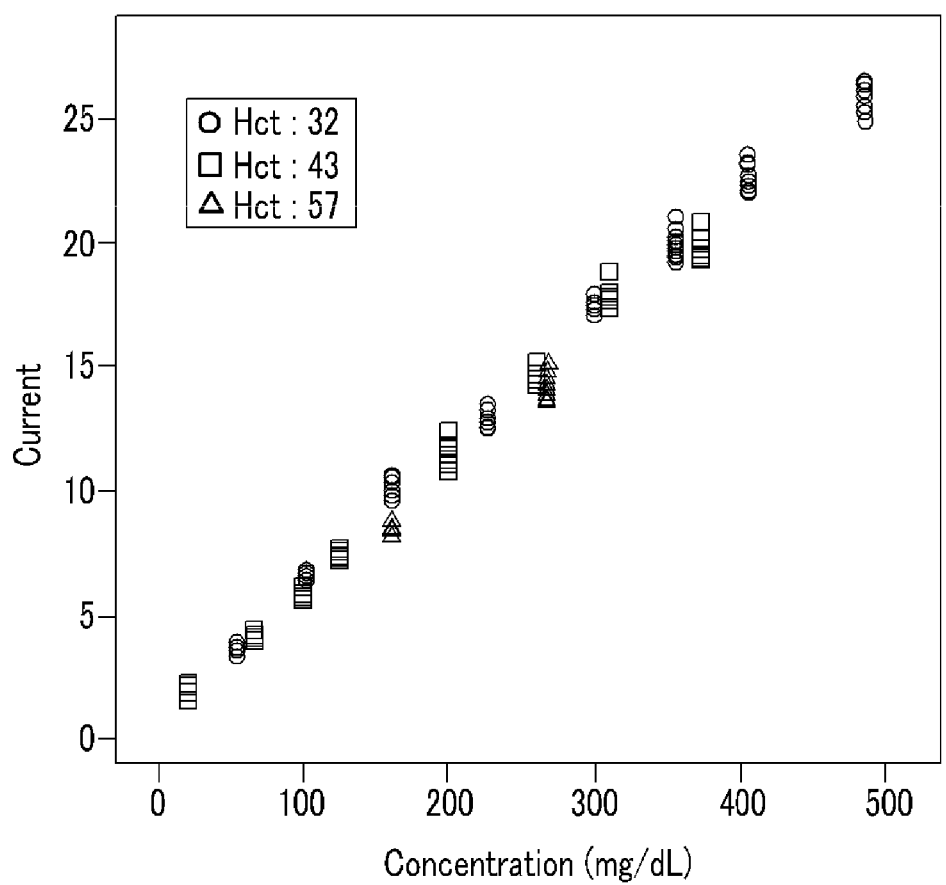
FIG. 20 is a graph showing the results of measurements made by varying the erythrocyte volume and the glucose concentration after compatibilizing the mediator.

FIG. 19 is a graph showing the measurement results obtained at different glucose concentrations, by applying the solution A onto the biosensor and then varying the hematocrit (Hct) of the blood to 37, 43, and 61%, while FIG. 20 is a graph showing the measurement results obtained at different glucose concentrations, by applying the solution B onto the biosensor and then varying the hematocrit of the blood to 32, 43, and 57%.

Here, the average amount introduced to 100 biosensors was 0.6, and a graph showing little impact of the blood type due to the interaction of the mediator was obtained. In FIG. 19, the average coefficient of variation (CV) at each concentration had a value of 5% or greater, while in FIG. 20, the coefficient of variation had a value of 3% or less. As such, it can be seen that when microcrystalline cellulose, tricaprylmethyl ammonium chloride, and a soap were further added, the accuracy of measurement was improved.

As described above, the biosensor has effects of significantly reducing the amount of a sample, allowing two or more measurements, and being applicable to the measurement of two or more target materials. Furthermore, accurate measurement is made possible by using a compatibilized mediator.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A biosensor that is configured to be inserted into a display device and measures a material contained in a sample, the biosensor comprising:
    first and second substrates that are opposed to each other and comprise a long edge, and a short edge that shares a corner of the biosensor and neighbors the long edge;
    a sample guiding layer;
    a penetrated opening that penetrates the first substrate, the sample guiding layer, and the second substrate;
    a first electrode that is located between the first substrate and the sample guiding layer;
    a second electrode that is located between the first substrate and the sample guiding layer, and spaced apart from the first electrode;
    a third electrode that is located between the sample guiding layer and the second substrate;

a fourth electrode that is located on the first substrate wherein the fourth electrode is located closer to the display device than the first electrode when the biosensor is inserted into the display device;

wherein the sample guiding layer has two sample inlets and is located on the first substrate, wherein each of the two sample inlets correspond to the long edge and short edge, respectively, and the sample inlet corresponding to the long edge is located closer to the fourth electrode than the penetrated opening;

wherein first and second sample guiding channels connect the two sample inlets, wherein the first and second guiding channels are connected to the penetrated opening at both sides of the penetrated opening opposite to each other; and wherein the first guiding channel connects the sample inlet that corresponds to the short edge with the penetrated opening and the second guiding channel is bent and connects the sample inlet that corresponds to the long edge with the penetrated opening.

2. The biosensor of claim 1, wherein the display device comprises:
a first connector pin; and
a second connector pin that has a greater length than that of the first connector pin and is spaced apart from the first connector pin to be extended parallel to the first connector pin,
wherein the display device displays an error message when the first connector pin is connected to the fourth electrode and the second connector pin is connected to the first electrode.

3. The biosensor of claim 1, wherein the display device comprises:
a first connector pin; and
a second connector pin that has a greater length than that of the first connector pin and is spaced apart from the first connector pin to be extended parallel to the first connector pin,
wherein amount of the material is displayed when the first and second connector pins are electrically connected to the third electrode.

4. The biosensor of claim 1, wherein the at least one channel includes a plurality of channels and the channels are formed to extend parallel to each other,
wherein the first electrode comprises a first sample measuring unit that is formed between the channels to extend in a direction parallel to the channels, and
wherein the second electrode comprises a second sample measuring unit that is formed apart from the first sample measuring unit by a certain distance and is parallel thereto.

5. The biosensor of claim 1, wherein the first electrode comprises:
a first body portion;
a first connecting portion that is connected to the first body portion and neighbors the fourth electrode, the first connecting portion being configured to be electrically connected to the display device to be extended along a direction in which the biosensor is inserted into the display device; and
a sample contacting portion that is connected to the first connecting portion and is configured to contact the sample.

6. The biosensor of claim 5,
wherein the second electrode comprises two branched portions that meet with each of the two sample guiding channels,
wherein each of the two branched portions is spaced apart from the sample contacting portion, respectively, and
wherein each of the two branched portions is located to be closer to the hole than the sample contacting portion along the two sample guiding channels, respectively.

7. The biosensor of claim 5, wherein the third electrode comprises:
second body portion; and
second connecting portion that is connected to the second body portion, the second connecting portion being configured to be electrically connected to the display device and to be extended along a direction in which the biosensor is inserted into the display device,
wherein the first connecting portion and the second connecting portion are exposed to the outside in opposite directions to each other, and the second electrode is located between the first connecting portion and the second connecting portion.

8. The biosensor of claim 7, wherein the first connecting portion and the second connecting portion are located such that they are symmetrical to each other based on the second electrode along a direction that perpendicularly crosses the direction in which the biosensor is inserted into the display device.

9. The biosensor of claim 1, wherein the sample guiding layer further comprises a sample guiding channel that connects the sample inlet with the penetrated opening,
wherein a mediator is located in the sample guiding channel, the mediator comprising:
an enzyme that reacts with the material;
an electron transfer medium that transfers electrons generated from the enzyme; and
a dispersion stabilizer that disperses and stabilizes the enzyme and the electron transfer medium.

10. The biosensor of claim 9, wherein the enzyme is at least one selected from the group consisting of glucose oxidase, glucose dehydrogenase, alcohol oxidase, alcohol dehydrogenase, pyrroloquinone (PQQ), and nicotinamide adenine dinucleotide/hydrogen (NAD/NADH).

11. The biosensor of claim 9, wherein the electron transfer medium is at least one selected from the group consisting of ferrocene, quinone, cobalt, nickel, ruthenium, a ferricyan compound, rhodium, palladium, osmium, iridium, platinum, hexaamineruthenium(III) chloride, derivatives comprising these, and transition metals.

12. The biosensor of claim 9, wherein the dispersion stabilizer is at least one selected from the group consisting of polyvinyl alcohol, polyethylene oxide, polyethylene glycol, carboxymethyl cellulose, hydroxymethyl cellulose, 2-hydroxyethyl cellulose, hydroxypropyl cellulose, microcrystalline cellulose, polyvinyl pyrrolidone, polyvinylidene fluoride, polymethyl methacrylate, and styrene butyl rubber.

13. The biosensor of claim 9, wherein the mediator further comprises a phase transfer catalyst, and
the phase transfer catalyst comprises at least one selected from the group consisting of phosphonium-based reagents, crown ether-based reagents, ammonium-based reagents, and polyethylene glycol (PEG)-based reagents.

14. The biosensor of claim 9, wherein the mediator further comprises glucose oxidase, hexaammineruthenium(III) chloride, carboxymethyl cellulose, microcrystalline cellulose, tricaprylmethyl ammonium chloride, t-octylphenoxypolyethoxyethanol, and a soap.

15. The biosensor of claim 9, wherein the mediator further comprises a surfactant, wherein the surfactant comprises at least one selected from the group consisting of anionic surfactants, cationic surfactants, amphoteric surfactants, and nonionic surfactants.

16. The biosensor of claim 15, wherein the anionic surfactant comprises a soap or alkylbenzene sulfonate.

* * * * *